US010995361B2

(12) United States Patent
Chen et al.

(10) Patent No.: US 10,995,361 B2
(45) Date of Patent: *May 4, 2021

(54) MULTIPLEXED SIGNAL AMPLIFIED FISH VIA SPLINTED LIGATION AMPLIFICATION AND SEQUENCING

(71) Applicant: Massachusetts Institute of Technology, Cambridge, MA (US)

(72) Inventors: Fei Chen, Cambridge, MA (US); Asmamaw T. Wassie, Boston, MA (US); Shahar Alon, Cambridge, MA (US); Adam Henry Marblestone, Arlington, MA (US); Anubhav Sinha, Cambridge, MA (US); Andrew Payne, Cambridge, MA (US); Edward Stuart Boyden, Chestnut Hill, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 357 days.

This patent is subject to a terminal disclaimer.

(21) Appl. No.: 15/876,347

(22) Filed: Jan. 22, 2018

(65) Prior Publication Data

US 2018/0216161 A1    Aug. 2, 2018

Related U.S. Application Data

(60) Provisional application No. 62/449,202, filed on Jan. 23, 2017.

(51) Int. Cl.
| | |
|---|---|
| *C12Q 1/68* | (2018.01) |
| *C12Q 1/6806* | (2018.01) |
| *C12Q 1/6841* | (2018.01) |
| *C12Q 1/6811* | (2018.01) |
| *C12Q 1/682* | (2018.01) |
| *C12Q 1/6855* | (2018.01) |

(52) U.S. Cl.
CPC ........... *C12Q 1/6806* (2013.01); *C12Q 1/682* (2013.01); *C12Q 1/6811* (2013.01); *C12Q 1/6841* (2013.01); *C12Q 1/6855* (2013.01); *C12Q 2600/158* (2013.01); *C12Q 2600/16* (2013.01); *C12Q 2600/166* (2013.01)

(58) Field of Classification Search
CPC .................................................. C12Q 1/6806
See application file for complete search history.

(56) References Cited

U.S. PATENT DOCUMENTS

| | | | |
|---|---|---|---|
| 5,952,232 A | 9/1999 | Rothman | |
| 6,107,081 A | 8/2000 | Feeback et al. | |
| 6,271,278 B1 | 8/2001 | Park et al. | |
| 6,287,870 B1 | 9/2001 | Wardlaw | |
| 10,059,990 B2* | 8/2018 | Boyden | C12Q 1/6806 |
| 10,317,321 B2* | 6/2019 | Tillberg | G01N 1/36 |
| 10,364,457 B2* | 7/2019 | Wassie | G01N 1/36 |
| 2002/0176880 A1 | 11/2002 | Cruise et al. | |
| 2003/0120231 A1 | 6/2003 | Wang et al. | |
| 2004/0137527 A1 | 7/2004 | Sleytr et al. | |
| 2004/0248326 A1 | 12/2004 | Ziaie et al. | |
| 2005/0034990 A1 | 2/2005 | Crooks et al. | |
| 2005/0090016 A1 | 4/2005 | Rich et al. | |
| 2005/0169962 A1 | 8/2005 | Bhatia et al. | |
| 2005/0196702 A1 | 9/2005 | Bryant et al. | |
| 2006/0000767 A1* | 1/2006 | Trauger | B09C 1/002 210/503 |
| 2006/0003356 A1 | 1/2006 | Shaw et al. | |
| 2006/0110760 A1 | 5/2006 | Kim et al. | |
| 2006/0115146 A1 | 6/2006 | Ogura et al. | |
| 2006/0165912 A1 | 7/2006 | Koberstein et al. | |
| 2007/0023942 A1 | 2/2007 | Andino et al. | |
| 2007/0042954 A1 | 2/2007 | Chen et al. | |
| 2007/0134902 A1 | 6/2007 | Bertino et al. | |
| 2008/0261834 A1* | 10/2008 | Simon | C09K 8/516 507/221 |
| 2008/0286360 A1 | 11/2008 | Shoichet et al. | |

(Continued)

FOREIGN PATENT DOCUMENTS

| | | |
|---|---|---|
| CN | 104350372 A | 2/2015 |
| EP | 3159361 A1 | 4/2017 |

(Continued)

OTHER PUBLICATIONS

Chen F, Tillberg PW, Boyden ES. Expansion microscopy. Science. Jan. 30, 2015; 347(6221):543-8. (Year: 2015).*
Chen F, Wassie AT, Cote AJ, Sinha A, Alon S, Asano S, Daugharthy ER, Chang JB, Marblestone A, Church GM, Raj A, Boyden ES. Nanoscale imaging of RNA with expansion microscopy. Nat Methods. Aug. 2016; 13(8):679-84. Epub Jul. 4, 2016. (Year: 2016).*
Ke R, Mignardi M, Pacureanu A, Svedlund J, Botling J, Wählby C, Nilsson M. In situ sequencing for RNA analysis in preserved tissue and cells. Nat Methods. Sep. 2013; 10(9):857-60. Epub Jul. 14, 2013. (Year: 2013).*
Ke et al. Supplementary Information (2013) Nat Methods. 10(9):857-60. pp. 1-29. (Year: 2013).*

*Primary Examiner* — Gary Benzion
*Assistant Examiner* — Olayinka A Oyeyemi
(74) *Attorney, Agent, or Firm* — Elmore Patent Law Group, P.C.; Carolyn Elmore; Joseph Zucchero

(57) ABSTRACT

The present invention relates to a method for amplifying at least one target RNA in a fixed and, optionally, expanded biological sample. In an embodiment of the invention, the method comprises incubating the fixed biological sample with a pair of polynucleotides complementary to non-overlapping and proximal sequences of a target RNA, wherein the polynucleotide pair hybridizes to the target RNA; ligating the polynucleotide pair using a ligase; and amplifying the ligation product. The invention further provides methods for detecting and optionally quantifying and/or sequencing the amplification product. As the method comprises hybridizing polynucleotide pairs to a target RNA in a fixed biological sample, the target RNA can be hybridized in situ.

15 Claims, 22 Drawing Sheets

Specification includes a Sequence Listing.

(56) References Cited

U.S. PATENT DOCUMENTS

| | | | |
|---|---|---|---|
| 2009/0011141 | A1 | 1/2009 | Carter et al. |
| 2009/0011420 | A1 | 1/2009 | Barron et al. |
| 2009/0096133 | A1 | 4/2009 | Doyle et al. |
| 2009/0191627 | A1 | 7/2009 | Fadeev et al. |
| 2009/0241681 | A1 | 10/2009 | Machauf et al. |
| 2010/0041128 | A1 | 2/2010 | Barnes et al. |
| 2010/0055161 | A1 | 3/2010 | Ahn |
| 2010/0056445 | A1 | 3/2010 | Sharma et al. |
| 2010/0068725 | A1 | 3/2010 | Armbruster et al. |
| 2010/0096334 | A1* | 4/2010 | Edmiston ............ C02F 1/705 210/691 |
| 2010/0119755 | A1 | 5/2010 | Chung et al. |
| 2011/0070604 | A1 | 3/2011 | Gimzewski et al. |
| 2011/0087315 | A1 | 4/2011 | Richardson-Burns et al. |
| 2011/0091717 | A1 | 4/2011 | Weiss et al. |
| 2011/0091922 | A1 | 4/2011 | Krishnan et al. |
| 2011/0291357 | A1 | 12/2011 | Boyle |
| 2012/0025271 | A1 | 2/2012 | Nakano |
| 2012/0184670 | A1 | 7/2012 | Kobayashi et al. |
| 2012/0220478 | A1 | 8/2012 | Shaffer |
| 2012/0251527 | A1 | 10/2012 | Reiser |
| 2012/0310223 | A1 | 12/2012 | Knox et al. |
| 2013/0045503 | A1 | 2/2013 | Miyawaki et al. |
| 2013/0203605 | A1 | 8/2013 | Shendure et al. |
| 2014/0087139 | A1 | 3/2014 | Rowley et al. |
| 2014/0193651 | A1 | 7/2014 | Kharlampieva et al. |
| 2014/0364330 | A1 | 12/2014 | Mershin et al. |
| 2015/0370961 | A1 | 12/2015 | Zhang et al. |
| 2015/0376261 | A1 | 12/2015 | Steyaert et al. |
| 2016/0116384 | A1* | 4/2016 | Chen ................ G01N 1/30 435/7.1 |
| 2016/0252528 | A1 | 9/2016 | Sangaralingham et al. |
| 2016/0304952 | A1* | 10/2016 | Boyden ............ C12Q 1/6874 |
| 2016/0305856 | A1* | 10/2016 | Boyden ............ G01N 33/582 |
| 2017/0067096 | A1* | 3/2017 | Wassie ............ C12Q 1/6806 |
| 2017/0087489 | A1 | 3/2017 | Rodrigues et al. |
| 2017/0089811 | A1 | 3/2017 | Tillberg et al. |
| 2017/0182220 | A1 | 6/2017 | Song et al. |

FOREIGN PATENT DOCUMENTS

| | | | |
|---|---|---|---|
| JP | 2005291759 | A | 10/2005 |
| JP | 2006036957 | A | 2/2006 |
| JP | 2008286694 | A | 11/2008 |
| JP | 2009191125 | | 8/2009 |
| JP | 2014-005231 | | 1/2014 |
| WO | 0008212 | A1 | 2/2000 |
| WO | 2007103665 | A2 | 9/2007 |
| WO | 2008058302 | A1 | 5/2008 |
| WO | 2010048605 | A1 | 4/2010 |
| WO | 2012142664 | A1 | 10/2012 |
| WO | 2014025392 | A1 | 2/2014 |
| WO | WO-2014025392 | A1 * | 2/2014 |
| WO | 2014152984 | A1 | 9/2014 |
| WO | 2015041755 | A1 | 3/2015 |
| WO | 2015127183 | A2 | 8/2015 |
| WO | 2016040489 | A1 | 3/2016 |
| WO | 2017027367 | A1 | 2/2017 |
| WO | 2017027368 | A1 | 2/2017 |
| WO | 2017079406 | A1 | 5/2017 |

OTHER PUBLICATIONS

Lee et al. Highly multiplexed subcellular RNA sequencing in situ. Science. Mar. 21, 2014; 343(6177):1360-1363. (Year: 2014).*

Park YN, Abe K, Li H, Hsuih T, Thung SN, Zhang DY. Detection of hepatitis C virus RNA using ligation-dependent polymerase chain reaction in formalin-fixed, paraffin-embedded liver tissues. Am J Pathol. Nov. 1996; 149(5):1485-91. (Year: 1996).*

Park, Y.N., "Detection of Hepatitis C Virus RNA Using Ligation-Dependent Polymerase Chain Reaction in Formalin Fixed, Paraffin-Embedded Liver Tissues," American Journal of Pathology, 149(5): pp. 1485-1491 (1996).

Cao, W., "DNA Ligases and Ligase-Based Technologies," Clinical and Applied Immunology Reviews, vol. 2(1): pp. 33-43 (2001).

Nilsson, M., et al., "RNA-Templated DNA Ligation for Transcript Analysis," Nucleic Acids Research, 29(2): pp. 578-581 (2001).

"Epitope Recovery Methods for IHC", Nov. 7, 2015, ThermoFisher Scientific, pp. 1-2.

Al, H. et al., "Exploration of new chromophore structures leads to the identification of improved blue fluorescent proteins", Biochemistry, 46, 2007, 5904-10.

Bates, M. et al., "Multicolor super-resolution imaging with photo-switchable fluorescent probes", Science, 317, 2007, 1749-1753.

Batish, M. et al., "Neuronal mRNAs Travel Singly into Dendrites", PNAS, vol. 109(12), 012, 4645-4650.

Beliveau, B. et al., "Versatile design and synthesis platform for visualizing genomes with Oligopaint FISH probes", PNAS, vol. 109(52): pfa, 2012, 21301-21306.

Bokman, S. H. et al., "Renaturation of Aequorea gree-fluorescent protein", Biochem. Biophys. Res. Commun., 101, 1981, 1372-80.

Bossi, M. et al., "Multicolor far-field fluorescence nanoscopy through isolated detection of distinct molecular species", Nano Lett., 8, 2008, 2463-8.

Bruchez, M. et al., "Semiconductor nanocrystals as fluorescent biological labels", Science, vol. 281, 1998, 2013-6.

Buckley, P. et al., "Cytoplasmic Intron Sequence-Retaining Transcripts Can Be Dendritically Targeted via ID Element Retrotransposons", Neuron, vol. 69, 2011, 877-884.

Buenrostro, J. D. et al., "ATAC-seq: A Method for Assaying Chromatin Accessibility Genome-Wide : ATAC-seq for Assaying Chromatin Accessibility", In: "Current Protocols in Molecular Biology", Wiley, New York, NY, Jan. 5, 2015.

Buxbaum, A. et al., "Single-Actin mRNA Detection in Neurons Reveals a Mechanism for Regulating Its Translatability", Science, vol. 343, 2014, 419-422.

Cabili, M. et al., "Localization and abundance analysis of human lncRNAs at single-cell and single-molecule resolution", Genome Biology, vol. 16(20), 2015.

Cai et al., Nat Meth., 10, 2013, 540-547.

Cajigas, I. et al., "The local transcriptome in the synaptic neuropil revealed by deep sequencing and high-resolution imaging", Neuron 74, 2012, 453-466.

Carpenter, A. E. et al., "CellProfiler: image analysis software for identifying and quantifying cell phenotypes", Genome Biol., 7, 2006, R100.

Chang, J-B et al., "Iterative expansion microscopy", Nature Methods, 14(6), Jun. 2017, 593-599.

Chen, F. et al., "Expansion Microscopy", Science, 347(6621): Jan. 15, 2015, 1-18.

Chen, F. et al., "Nanoscale Imaging of RNA with Expansion Microscopy", Nature Methods, 13(8): Aug. 2016, 679-684.

Chen, F. et al., "Supplementary Material for Expansion Microscopy", Science, 347(6221), Jan. 15, 2015, 543-548.

Chen et al., "Spatially resolved, highly multiplexed RNA profiling in single cells", Science. vol. 348(6233), 2015, aaa6090-aaa6090.

Chen, X. et al., "[Supplementary material] ATAC-see reveals the accessible genome by transposase-mediated imaging and sequencing", Nature Methods, vol. 13, No. 12, Oct. 17, 2016, 1813-1828.

Choi et al., "Next-Generation in Situ Hybridization Chain Reaction: Higher Gain, Lower Cost, Greater Durability", ACS Nano 8(5), 2014, 4284-4294.

Choi, H. et al., "Programmable in situ amplification for multiplexed imaging of mRNA expression", Nature Biotechnology, 28(11), 2010, 1208-1212.

Chozinski, T. et al., "Expansion microscopy with conventional antibodies and fluorescent proteins", Nature Methods, vol. 13(6), 2016, 485-491.

Chu et al., "Non-invasive intravital imaging of cellular differentiation with a bright red-excitable fluorescent protein", Nat. Methods, 11, 2014, 572-8.

Clemson, C. et al., "An architectural role for a nuclear noncoding RNA: NEAT1 RNA is essential for the structure of paraspeckles", Molecular Cell, 33, 2009, 717-26.

Cormack, B. P. et al., "FACS-optimized mutants of the green fluorescent protein (GFP)", Gene, 173, 1996, 33-8.

(56) References Cited

OTHER PUBLICATIONS

Cubitt, A. B. et al., "Understanding structure-function relationships in the Aequorea victoria green fluorescent protein", Methods Cell Biol., 58, 1999, 19-30.
Dedecker, P. et al., "Localizer: fast, accurate, open-source, and modular software package for superresolution microscopy", J. Biomed. Opt., 17, 2012, 126008.
Edelstein, A. et al., "Computer control of microscopes using µManager", Curr. Protoc. Mol. Biol. Chapter 14, Unit14.20, 2010.
English, B. P. et al., "A three-camera imaging microscope for high-speed single-molecule tracking and super-resolution imaging in living cells", in SPIE Nanosci. + Eng. (Mohseni, H., Agahi, M. H. & Razeghi, M.) 955008 (International Society for Optics and Photonics, 2015). doi:10.1117/12.2190246.
Engreitz, J. et al., "The Xist lncRNA exploits three-dimensional genome architecture to spread across the X chromosome", Science 341, 2013, 1237973.
Femino, A. et al., "Visualization of Single RNA Transcripts in Situ", Science, vol. 280, 1998, 585-590.
Feng, G. et al., "Imaging neuronal subsets in transgenic mice expressing multiple spectral variants of GFP", Neuron, 28, 2000, 41-51.
Filonov, G. S. et al., "Bright and stable near-infrared fluorescent protein for in vivo imaging", Nat. Biotechnol., 29, 2011, 757-61.
Fouz, M. et al., "Bright Fluorescent Nanotags from Bottlebrush Polymers with DNA-Tipped Bristles", ACS Central Science, vol. 1, 2015, 431-438.
Freifeld, L. et al., "Expansion microscopy of zebrafish for neuroscience and developmental biology studies", PNAS (online), Nov. 21, 2017, E10799-E10808.
Goedhardt, J. et al., "Structure-guided evolution of cyan fluorescent proteins towards a quantum yield of 93%", Nat. Commun., 3, 2012, 751.
Griesbeck, O. et al., "Reducing the environmental sensitivity of yellow fluorescent protein. Mechanism and applications", J. Biol. Chem., 276, 2001, 29188-94.
Gurskaya, N. G. et al., "Engineering of a monomeric green-to-red photoactivatable fluorescent protein induced by blue light", Nat. Biotechnol., 24, 2006, 461-5.
Habuchi, S. et al., "mKikGR, a monomeric photoswitchable fluorescent protein", PLoS One, 3, 2008, e3944.
Hackstadt, T., "Steric hindrance of antibody binding to surface proteins of Coxiella burnetti by phase I lipopolysaccharide", Infect Immun, 56, 1998, 802-807.
Heim, R. et al., "Engineering green fluorescent protein for improved brightness, longer wavelengths and fluorescence resonance energy transfer", Curr. Biol., 6, 1996, 178-82.
Heim, R. et al., "Wavelength mutations and posttranslational autoxidation of green fluorescent protein", Proc. Natl. Acad. Sci. U.S.A., 91, 1994, 12501-4.
Huang, B. et al., "Whole-cell 3D STORM reveals interactions between cellular structures with nanometer-scale resolution", Nat. Methods, 5, 2008, 1047-1052.
Huisken, J. et al., "Optical Sectioning Deep Inside Live Embryos by Selective Plane Illumination Microscopy", Science. vol. 305, 2004, 1007-1009.
Hunt, et al., "High temperature antigen retrieval and loss of nuclear morphology: a comparison of microwave\rand autoclave techniques", J. Clin. Pathol. 49, 1996, 767-770.
Jekel, P A. et al., "Use of endoproteinase Lys-C from Lysobacter enzymogenes in protein sequence analysis", Anal. Biochem., 134, 1983, 347-354.
Jimenez, N. et al., "A Novel Approach for Intracellular 3D Immuno-Labeling for Electron Tomography", Traffic,13, 2012, 926-933.
Jung, H. et al., "Axonal mRNA localization and local protein synthesis in nervous system assembly, maintenance and repair", Nat. Rev. Neurosci., vol. 13(5), 2012, 308-24.

Kakimoto, K. et al., "Hypothesis for the mechanism for heat-induced antigen retrieval occurring on fresh frozen sections without formalin-fixation in immunohistochemistry", J Mol Histol., 39, 2008, 389-399.
Kaur, et al., Biochemistry 45, 2006, 7347-7355.
Ke, R. et al., "In situ sequencing for RNA analysis in preserved tissue and cells", Nature Methods, vol. 10(9), 2013, 857-60.
Kroon, D.-J , "B-spline Grid, Image and Point based Registration", Matlab Cent. at <http://www.mathworks.com/matlabcentral/fileexchange/20057-b-spline-grid--image-and-point-based-registration>.
Laemmli, U. K., "Cleavage of structural proteins during the assembly of the head of bacteriophage T4", Nature, 227, 1970, 680-685.
Lam, A. J. et al., "Improving FRET dynamic range with bright green and red fluorescent proteins", Nat. Methods, 9, 2012, 1005-12.
Lee, J. et al., "Highly Multiplexed Subcellular RNA Sequencing in Situ", Duplicate—RefID 308986 Science, vol. 343, 2014, 1360-1363.
Lein, E. et al., "Genome-wide atlas of gene expression in the adult mouse brain", Nature, vol. 445, 2007, 168-76.
Levsky, J. et al., "Fluorescence in situ hybridization: past, present and future", Journal of Cell Science, 116, 2003, 2833-2838.
Lieberman-Aiden, E. et al., "Comprehensive mapping of long-range interactions reveals folding principles of the human genome", Science 326, 2009, 289-93.
Livet, J. et al., "Transgenic strategies for combinatorial expression of fluorescent proteins in the nervous system", Nature, 450, 2007, 56-62.
Lowe, D. G. , "Distinctive Image Features from Scale-Invariant Keypoints", Int. J. Comput. Vis., 60, 2004, 91-110.
Lubeck, E. et al., "Single-cell in situ RNA profiling by sequential hybridization", Nature Methods, vol. 11(4), 2014, 360-1.
Lubeck, E. et al., "Single-cell systems biology by super-resolution imaging and combinatorial labeling", Nature Methods, vol. 9, 2012, 743-8.
Markwardt, M. L. et al., "An improved cerulean fluorescent protein with enhanced brightness and reduced reversible photoswitching", PLoS One, 6, 2011, e17896.
Mckinney, S. A. et al., "A bright and photostable photoconvertible fluorescent protein", Nat. Methods, 6, 2009, 131-3.
Mito, M. et al., "Simultaneous multicolor detection of RNA and proteins using super-resolution microscopy", Methods, doi:10.1016/j.ymeth.2015.11.007., 2015.
Mortensen, K. I. et al., "Optimized localization analysis for singlemolecule tracking and super-resolution microscopy", Nat. Methods, 7, 2010, 377-81.
Nagai, T. et al., "A variant of yellow fluorescent protein with fast and efficient maturation for cell-biological applications", Nat. Biotechnol., 20, 2002, 87-90.
Nagre, R. D. et al., "Thermosaline Resistant Acrylamide-Based Polyelectrolyte as Filtration Control Additive in Aqueous-Based Mud", Petroleum and Coal, vol. 56, No. 3, 2014, 222-230.
Ormo, M. et al., "Crystal structure of the Aequorea victoria green fluorescent protein", Science, 273, 1996, 1392-5.
Panning, B. et al., "X chromosome Inactivation is Mediated by by Xist RNA stabilization", Cell. vol. 90, 1997, 907-16.
Plath, K. et al., "Xist RNA and the mechanism of X chromosome inactivation", Annu. Rev. Genet. 36, 2002, 233-78.
Raj, A. et al., "Detection of individual endogenous RNA transcripts in situ using multiple singly labeled probes", Methods in Enzymology, vol. 472 (Elsevier Inc.), 2010, 365-386.
Raj, A. et al., "Imaging individual mRNA molecules using multiple singly labeled probes", Nat. Methods 5(10), 2008, 877-879.
Randall, K. J. et al., "A dual-label technique for the immunohistochemical demonstration of T-lymphocyte subsets in formalin-fixed, paraffin-embedded rat lymphoid tissue", Toxicol. Pathol., 36, 2008, 795-804.
Rego, E. H. et al., "Nonlinear structured-illumination microscopy with a photoswitchable protein reveals cellular structures at 50-nm resolution", Proc. Natl. Acad. Sci. U.S.A., 109 2012, E135-43.
Reinhart-King, C. A. et al., "Dynamics and Mechanics of EndothelialCell Spreading", Biophysical J, 89(1):., Jul. 1, 2005, 676-689.
Rose, R. et al., "Ocular ascorbate transport and metabolism", A. Comp. Physiol.,100, 1991, 273-85.

(56) References Cited

OTHER PUBLICATIONS

Schindelin, J. et al., "Fiji: an open-source platform for biological-image analysis", Nature Methods, vol. 9, 2012, 676-82.
Schnell, U. et al., "Immunolabeling artifacts and the need for live-cell imaging", Nat. Methods, 9, 2012, 152-158.
Seneviratne, U. et al., "S-nitrosation of proteins relevant to Alzheimer's disease during early stages of neurodegeneration", Proc. Natl. Acad. Sci. U. S. A. 1521318113—(2016). doi:10.1073/pnas.1521318113.
Shah, S. et al., "Single-molecule RNA detection at depth via hybridization chain reaction and tissue hydrogel embedding and clearing", Development in Review, 2016.
Shaner, N. C. et al., "Improved monomeric red, orange and yellow fluorescent proteins derived from *Discosoma* sp. red fluorescent protein", Nat. Biotechnol., 22 2004, 1567-72.
Shaner, N. C. et al., "Improving the photostability of bright monomeric orange and red fluorescent proteins", Nat. Methods, 5, 2008, 545-51.
Shcherbakova, D. M., "An orange fluorescent protein with a large Stokes shift for single-excitation multicolor FCCS and FRET imaging", J. Am. Chem. Soc., 134, 2012, 7913-23.
Shcherbo, D. et al., "Far-red fluorescent tags for protein imaging in living tissues", Biochem. J., 418, 2009, 567-74.
Sniegowski, J. A. et al., "Maturation efficiency, trypsin sensitivity, and optical properties of Arg96, Glu222, and Gly67 variants of green fluorescent protein", Biochem. Biophys. Res. Commun., 332, 2005, 657-63.
Steward, O. et al., "Compartmentalized synthesis and degradation of proteins in neurons", Neuron, vol. 40, 2003, 347-359.
Steward, O. et al., "Synaptic activation causes the mRNA for the leg Arc to localize selectively near activated postsynaptic sites on dendrites", Neuron, vol. 21, 1998, 741-751.
Strack, R., "Imaging Bigger is Better for Super-Resolution", Nature Methods, 12(13), Mar. 1, 2015, 169.
Subach, F. V. et al., "Bright monomeric photoactivatable red fluorescent protein for two-color super-resolution sptPALM of live cells", J. Am. Chem. Soc., 132, 2010, 6481-91.
Subach, O. M. et al., "An Enhanced Monomeric Blue Fluorescent Protein with the High Chemical Stability of the Chromophore", PLoS One, 6, 2011, e28674.
Thevenaz, P. et al., "A pyramid approach to subpixel registration based on intensity", IEEE Trans. Image Process., 7, 1998, 27-41.
Tillberg, P. et al., "Protein-Retention Expansion Microscopy of Cells and Tissues Labeled Using Standard Fluorescent Proteins and Antibodies", Nature Biotechnology vol. 34(9), 2016, 987-995.
Vedaldi, A. et al., Vlfeat. in Proc. Int. Conf. Multimed.—MM '10 1469 (ACM Press, 2010). doi:10.1145/1873951.1874249.
Wachter, R. M. et al., "Sensitivity of the yellow variant of green fluorescent protein to halides and nitrate", Curr. Biol., 9, 1999, R628-R629.
Wang, F. et al., "RNAscope: A novel in situ RNA analysis platform for formalin-fixed, paraffin-embedded tissues", Journal of Molecular Diagnostics, vol. 14(1), 2012, 22-29.
Wu, C. C. et al., "A method for the comprehensive proteomic analysis of membrane proteins", Nat. Biotechnol., 21, 2003, 532-8.
Xingqi, C. et al., "ATAC-see reveals the accessible genome by transposase-mediated HJ, imaging and sequencing", Nature Methods, vol. 13, No. 12, Dec. 1, 2016, 1013-1020.
Zhang, D. et al., "Dynamic DNA nanotechnology using strand-displacement reactions", Nature Chemistry, vol. 3, 2011, 103-113.
Zimmerman, T. A. et al., "Adapting the stretched sample method from tissue profiling to imaging", Proteomics, 8, 2008, 3809-3815.
Van Vliet, et al., "The Biomechanics Toolbox: Experimental Approaches for Living Cells and Biomolecules," Acta Materialia, vol. 51, pp. 5881-5905 (Aug. 2003).
Office Action dated Apr. 4, 2018 from U.S. Appl. No. 14/627,310, filed Feb. 20, 2015.
Bi, X. et al., "In situ-forming cross-linking hydrogel systems: chemistry and biomedical applications", In: "Emerging Concepts in Analysis and Applications of Hydrogels", INTECH, Aug. 24, 2016, 131-158.
Breitwieser, A. et al., "Magnetic Beads Functionalized with Recombinant S-Layer Protein Exhibit High Human IgG-Binding and Anti-Fouling Properties", Current Topics in Peptide & Protein Research, vol. 17, 2016, 45-55.
Dilorenzo, F. et al., "Nanostructural Heterogeneity in Polymer Networks and Gels", Polymer Chemistry, vol. 6, 215, 5515-5528.
Goor, Olga J. et al., "Introduction of anti-fouling coutings at the surface of supramolecular elastomeric materials via post-modification of reactive supramolecular additives", Polymer Chem., vol. 8, No. 34, Jan. 1, 2017, 5228-5238.
Gyorvary, E. S. et al., "Self-Assembly and Recrystallization of Bacterial S-Layer Proteins at Silicon Supports Imaged in Real Time by Atomic Force Microscopy", Journal of Microscopy, vol. 212, 2003, 300-306.
Hoffman, T. L. et al., "A Biosensor Assay for Studying Ligand-Membrane Receptor Interactions: Binding of Antibodies and HIV-1 Env to Chemokine Receptors", PNAS, 97(21), 2000, 11215-11220.
Jiang, Y. et al., "Click hydrogels, microgels and nanogels: emerging platforms for drug delivery and tissue engineering", Biomaterials, vol. 35, No. 18, Jun. 1, 2014, 4969-4985.
Majcher, M. J. et al., "Hydrogel synthesis and design", In: "Cellulose-Based Superabsorbent Hydrogels", Springer International Publishing, Jan. 1, 2018, 1-41.
Orakdogen, N. et al., "Correlation Between Crosslinking Efficiency and Spatial Inhomogeneity in Poly(acrylamide) Hydrogels", Polymer Bulletin, vol. 57, 2006, 631-641.
Oshima, K. et al., "Model Polyelectrolyte Gels Synthesized by End-Linking of Tetra-Arm Polymers with Click Chemistry: Synthesis and Mechanical Properties", Macromolecules, vol. 47, 2014, 7573-7580.
Pum, D. et al., "Reassembly of S-Layer Proteins", Nanotechnology, 2014, 1-15.
Rothbauer, M. et al., "Exploitation of S-Layer Anisotropy: pH-Dependent Nanolayer Orientation for Cellular Micropatterning,", Acs NANO, published online, 2013.
Sakai, T. et al., "Design and Fabrication of a High-Strength Hydrogel with Ideally Homogenous Network Structure from Tetrahedron-Like Macromonomers", Macromolecules, vol. 41, 2008, 5379-5384.
Sleytr, U. et al., "Heterologous Reattachment of Regular Arrays of Glycoproteins on Bacterial Surfaces", Nature, vol. 257, 1975, 400-401.
Sleytr, U. et al., "S-Layers Principles and Applications", FEMS Microbiology Rev., 2014, 1-42.
Xu, J. et al., "Bioorthogonally cross-linked hydrogel network with precisely controlled disintegration time over a broad ragne", J. Am. Chem.Soc., vol. 136, No. 11, Mar. 19, 2014, 4105-4108.
Yazici, I. et al., "Spatial Inhomogeneity in Poly(acrylic acid) Hydrogels", Polymer, vol. 46, 2005, 2595-2602.
Zhang, R. et al., "Tools for GPCR Drug Discovery", Acta Pharmacologica Sinica, 33, 2012, 372-384.
Zhou, C. et al., "Synthesis and characterization of well-defined PAA-PEG multi-responsive hydrogels by ATRP and click chemistry", RSC ADV., vol. 4, No. 97, Jan. 1, 2014, 54631-54640.

\* cited by examiner

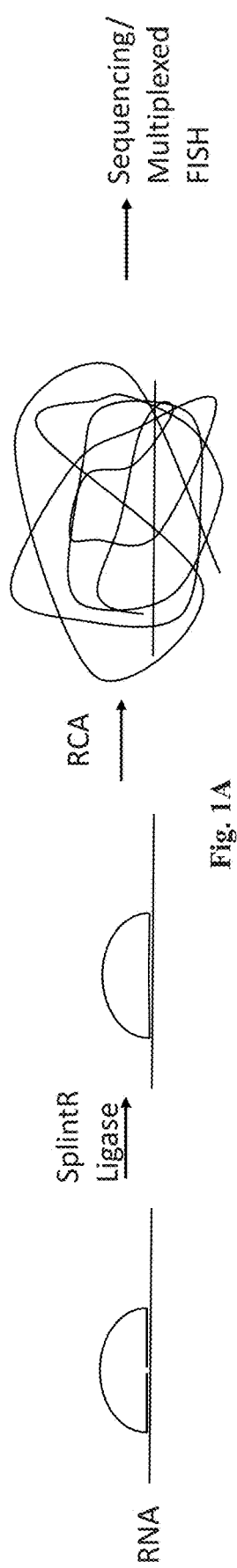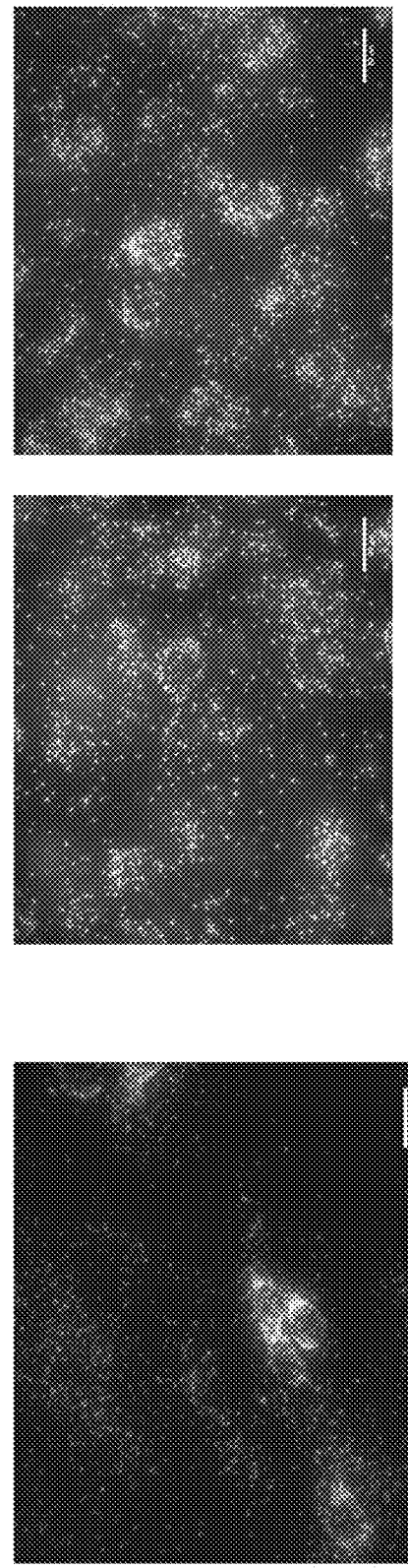
Fig. 1A
Fig. 1B
Fig. 1C

MULTIPLEXED SIGNAL AMPLIFIED FISH VIA SPLINTED LIGATION AMPLIFICATION AND SEQUENCING

RELATED APPLICATION

This application claims the benefit of U.S. Provisional Application No. 62/449,202, filed on Jan. 23, 2017. The entire teachings of the above application are incorporated herein by reference.

STATEMENT REGARDING FEDERALLY SPONSORED RESEARCH OR DEVELOPMENT

This invention was made with U.S. government support under Grant Number NYSCF-R-NI10, awarded by NYSCF; Grant Number 5-DPI0NS087724M, awarded by National Institute of Health; Grant Number 134062-5093041, awarded by Army Research Office, Synthetic Brain Project; Grant Number 152772.5906243.0105, awarded by National Institute of Health; Grant Number 4R01MH103910, awarded by National Institute of Health; Grant Number FP053369-N, awarded by University of Chicago; and Grant Number 5-025836-00001, awarded by Life Sciences Research Foundation. The government has certain rights in this invention.

BACKGROUND

When biological material, such as, for example, a tissue fragment or isolated cells, is removed from a living organism, the cells die within a short period of time. The dead cells are then broken down first by autolysis/fermentation and then bacterially, so that the original cell and tissue structures, components or molecules are destroyed. If cells or tissue fragments are to be removed from an organism for histological examination, it is recommended to fix the biological sample taken to prevent degradation. Fixation leaves the structures of the sample substantially unchanged to allow histological assessment thereof. Additionally, fixation allows long-term preservation and archiving of the samples. For these reasons, many morphological examinations are only possible based on fixed material.

Fixation is regularly achieved by protein-precipitating or protein-crosslinking compounds such as acids, alcohols, ketones or other organic substances such as glutaraldehyde or formaldehyde. Fixation with formaldehyde (employed e.g. in the form of a 35 percent by weight aqueous solution referred to as "formalin") followed by embedding the fixed material in paraffin (called "formalin-fixed, paraffin-embedded" (FFPE) material) has importance in particular in pathology.

The disadvantage of fixation with cross-linking fixatives such as formaldehyde is that it is very difficult to isolate biomolecules such as, DNA, RNA or proteins from respectively fixed material. Crosslinking occurs between the fixative, such as formaldehyde, and proteins as well as other biomolecules, including the nucleic acids, present in the sample making the release and isolation of the nucleic acids (DNA or RNA) from fixed samples difficult. For investigations on a molecular level, in particular for clinical or diagnostic applications, analysis of the nucleic acids is of great importance. Numerous methods have been developed for releasing and isolating nucleic acids from fixed samples to allow analysis. However, such methods do not allow for analyzing nucleic acids or localizing them in situ within a cell or tissue.

Therefore, it would be advantageous to analyze nucleic acids in the native state of cells and tissues without the need to release and isolate nucleic acids from fixed samples.

SUMMARY

The present invention further relates to a method for amplifying at least one target RNA in a fixed and, optionally, expanded biological sample. In an embodiment of the invention, the method comprises incubating the fixed biological sample with a pair of polynucleotides complementary to non-overlapping and proximal sequences of a target RNA, wherein the polynucleotide pair hybridizes to the target RNA; ligating the polynucleotide pair using a ligase; and amplifying the ligation product.

The present invention further relates to a method for detecting at least one target RNA in a fixed and, optionally, expanded biological sample. In an embodiment of the invention, the method comprises incubating the fixed biological sample with a pair of polynucleotides complementary to non-overlapping and proximal sequences of a target RNA, wherein the polynucleotide pair hybridizes to the target RNA; ligating the polynucleotide pair using a ligase; amplifying the ligation product; and detecting and optionally quantifying the amplification product.

As the methods disclosed herein comprises hybridizing polynucleotide pairs to a target RNA in a fixed biological sample, the target RNA can be hybridized in situ.

The methods may further comprises localizing the target RNA within the sample.

The methods may further comprises sequencing the target RNA within the sample.

BRIEF DESCRIPTION OF THE DRAWINGS

Other aspects, advantages and novel features of the invention will become more apparent from the following detailed description of the invention when considered in conjunction with the accompanying drawings wherein:

FIG. 1A through 1C depict an embodiment of an RCA based multiplexed FISH workflow according to the invention. (A) Work flow for RCA based multiplexing. (B) Wide-field image showing FISH staining (green and red) in ExM-treated cultured primary hippocampal neurons after targeting ActB transcripts with padlock probes followed by SplintR ligase based ligation and RCA amplification. Scale bar, 50 µm. (C) Wide-field image showing RCA based FISH staining (green and red) performed against ActB in expanded Thy1-YFP (blue) cortical brain slices. Scale bars, 50 µm. All images are maximum intensity projections.

DETAILED DESCRIPTION

Figure 2:
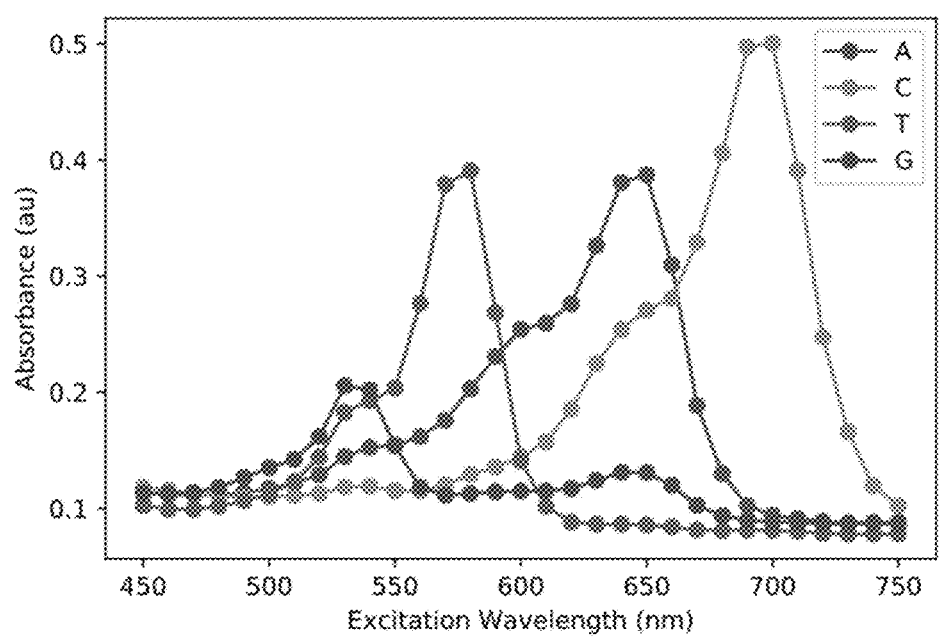
FIG. 2. Measurement of emission and absorption spectra for MiSeq dyes. (a) Absorption spectra for MiSeq dyes indicating four unique colors. (b) Emission spectra for an excitation close to each of the absorption maxima.
Figure 2:
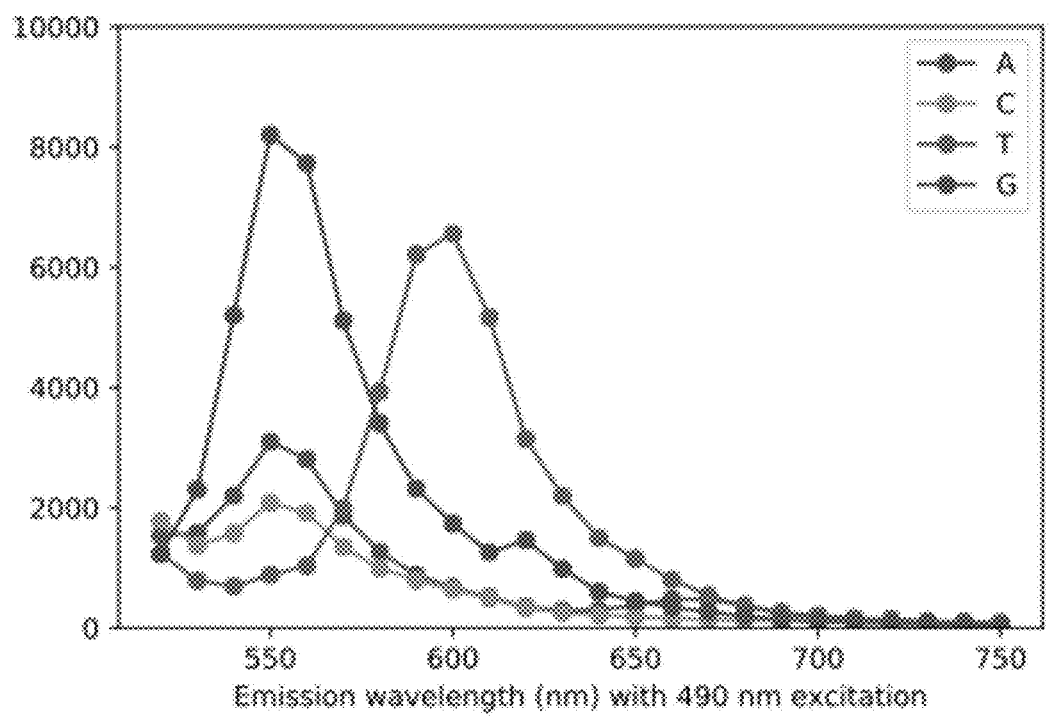
Figure 2:
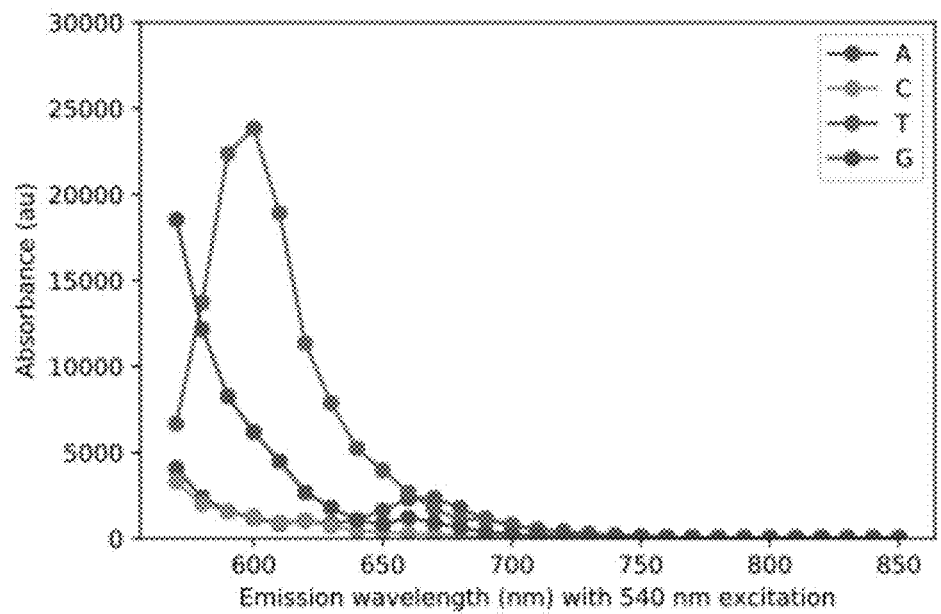
Figure 2:
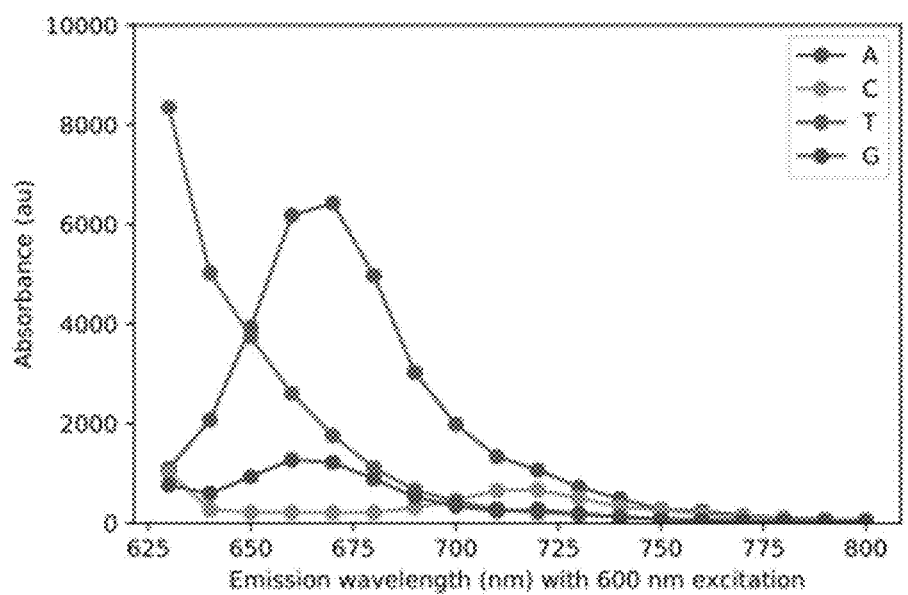
Figure 2:
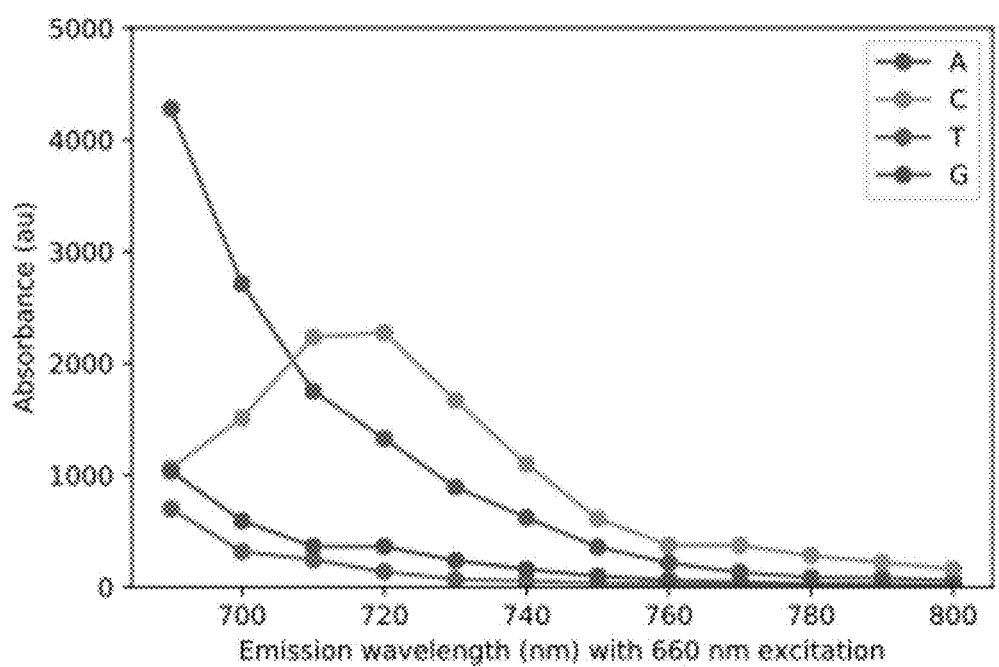

As used herein and in the appended claims, the singular forms "a", "an", and "the" are defined to mean "one or more" and include the plural unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

The present invention provides a method for amplifying at least one target RNA in a fixed and, optionally, expanded biological sample. In an embodiment of the invention, the method comprises the steps: (a) fixing a biological sample; (b) optionally expanding the biological sample, (c) incubating the biological sample with a pair of polynucleotides complementary to non-overlapping and proximal sequences of a target RNA, wherein the polynucleotide pair hybridizes to the target RNA; (d) ligating the polynucleotide pair using a ligase; and (e) amplifying the ligation product.

The method disclosed herein may further comprise quantifying the amplification product. The method disclosed herein may further comprise sequencing the amplification product.

The present invention provides a method for amplifying at least one target RNA in a fixed and, optionally, expanded biological sample. In an embodiment of the invention, the method comprises the steps: (a) incubating the biological sample with a pair of polynucleotides complementary to non-overlapping and proximal sequences of a target RNA, wherein the polynucleotide pair hybridizes to the target RNA; (b) ligating the polynucleotide pair using a ligase; and (c) amplifying the ligation product.

The method disclosed herein may further comprise quantifying the amplification product. The method disclosed herein may further comprise sequencing the amplification product.

The present invention further provides a method for detecting at least one target RNA in a fixed and, optionally, expanded biological sample. In an embodiment of the invention, the method comprises the steps: (a) fixing a biological sample; (b) optionally expanding the biological sample, (c) incubating the biological sample with a pair of polynucleotides complementary to non-overlapping and proximal sequences of a target RNA, wherein the polynucleotide pair hybridizes to the target RNA; (d) ligating the polynucleotide pair using a ligase; (e) amplifying the ligation product; (f) detecting the amplification product (g) optionally quantifying the amplification product. In one embodiment, the method further comprises the step of (h) localizing the target RNA within the sample.

The present invention provides a method for detecting at least one target RNA in a fixed and, optionally, expanded biological sample. In an embodiment of the invention, the method comprises the steps: (a) incubating the biological sample with a pair of polynucleotides complementary to non-overlapping and proximal sequences of a target RNA, wherein the polynucleotide pair hybridizes to the target RNA; (b) ligating the polynucleotide pair using a ligase; (c) amplifying the ligation product; (d) detecting the amplification product (e) optionally quantifying the amplification product. In one embodiment, the method further comprises the step of (f) localizing the target RNA within the sample.

As the methods disclosed herein comprises hybridizing polynucleotide pairs to a target RNA in a fixed biological sample, the target RNA can be hybridized in situ. As used herein, the terms "hybridized in situ" or "in situ hybridization" refer to a technique for localizing specific nucleic acid targets within fixed tissues and cells, providing temporal and spatial information about gene expression and genetic loci.

The term "fixed biological sample" is used herein in a broad sense and is intended to include sources that contain nucleic acids and can be fixed. Exemplary biological samples include, but are not limited to, tissues including but not limited to, liver, spleen, kidney, lung, intestine, thymus, colon, tonsil, testis, skin, brain, heart, muscle and pancreas tissue. Other exemplary biological samples include, but are not limited to, biopsies, bone marrow samples, organ samples, skin fragments and organisms. Materials obtained from clinical or forensic settings are also within the intended meaning of the term biological sample. Preferably, the sample is derived from a human, animal or plant. Preferably, the biological sample is a tissue sample, preferably an organ tissue sample. Preferably, samples are human. The sample can be obtained, for example, from autopsy, biopsy or from surgery. It can be a solid tissue such as, for example, parenchyme, connective or fatty tissue, heart or skeletal muscle, smooth muscle, skin, brain, nerve, kidney, liver, spleen, breast, carcinoma (e.g. bowel, nasopharynx, breast, lung, stomach etc.), cartilage, lymphoma, meningioma, placenta, prostate, thymus, tonsil, umbilical cord or uterus. The tissue can be a tumor (benign or malignant), cancerous or precancerous tissue. The sample can be obtained from an animal or human subject affected by disease or other pathology or suspected of same (normal or diseased), or considered normal or healthy. As used herein, the term "fixed biological sample, explicitly excludes cell-free samples, for example cell extracts, wherein cytoplasmic and/or nuclear components from cells are isolated.

Fixation of the biological sample can be effected with fixatives known to the person skilled in the art. In one embodiment, the fixative, includes but is not limited to, acids, alcohols, ketones or other organic substances, such as, glutaraldehyde, formaldehyde or paraformaldehyde. Examples of fixatives and uses thereof may be found in Sambrook et al. (2000); Maniatis et al. (1989). Preferably, the used fixation also preserves DNA and RNA. According to one embodiment of the process according to the invention, a formaldehyde-fixed, paraffin-embedded biological sample (FFPE sample) is used. Other fixatives and fixation methods for providing a fixed biological sample are known in the prior art. For example, the biological sample can be fresh froze, wherein alcohol based fixed samples can be used. In one embodiment, the fixed tissue may or may not be embedded in a non-reactive substance such as paraffin. Embedding materials include, but are not limited to, paraffin, mineral oil, non-water soluble waxes, celloidin, polyethylene glycols, polyvinyl alcohol, agar, gelatine, nitrocelluloses, methacrylate resins, epoxy resins or other plastic media. Thereby, one can produce tissue sections of the biological material suitable for histological examinations.

Alternatively or additionally, the fixed biological sample can be an expandable biological sample. An expandable biological sample can be effected by embedding the sample in a swellable material that has been perfused throughout the sample as described by Chen et al. (Chen et al., *Science*, 347, 543 (2015) and U.S. Patent Publication Nos. US 2016-0116384-A1; US 2016-0305856-A1; US 2016-0304952-A1; and U.S. patent application Ser. Nos. 15/229,539 and 15/229,545 incorporated herein by reference in their entirety). Briefly, a sample, such as tissue, can be permeabilized. A permeabilized sample can be infused with monomers or precursors of a swellable material and then causing the monomers or precursors to undergo polymerization within the sample to form the swellable material. During or after polymerization, the swellable material can be anchored or cross-linked (e.g., covalently crosslinked) to the sample. The sample-swellable material complex is optionally treated with protease to homogenize the mechanical characteristics of the sample. The sample-swellable material complex can then be treated by dialysis in a solvent or liquid, such as in water, resulting in isotropic physical expansion of the sample. In this manner, the fixed biological sample is physically "enlarged", or "expanded", as compared to the biological sample before swelling.

An expandable biological sample can also be prepared by contacting the sample with a bi-functional linker comprising a binding moiety and an anchor, wherein the binding moiety binds to target nucleic acids in the sample; permeating the sample with a composition comprising precursors of a swellable material; and initiating polymerization to form a swellable material, wherein the swellable material is bound to the small molecule linker or a nucleic acid adaptor to form a sample-swellable material complex.

As used herein a bi-functional linker comprises reactive groups to functional groups (e.g., primary amines or sulfhydryls) on biomolecules within the sample. The bi-functional linker may be used to chemically modify the amine group of biomolecules with a swellable polymer functional group, which enables target nucleic acids within the sample to be directly anchored to, or incorporated into, the swellable polymer. In one embodiment, the bifunctional linker is a hetero-bifunctional linker. Hetero-bifunctional linkers possess different reactive groups at either end of a spacer arm, i.e., atoms, spacers or linkers separating the reactive groups. These reagents not only allow for single-step conjugation of molecules that have the respective target functional group, but they also allow for sequential (two-steps) conjugations that minimize undesirable polymerization or self-conjugation. The bi-functional linker may be a small molecule linker or a nucleic acid adaptor.

The anchor may be a physical, biological, or chemical moiety that attaches or crosslinks the sample to the composition, hydrogel or other swellable material. This may be accomplished by crosslinking the anchor with the swellable material, such as during or after the polymerization, i.e., in situ formation of the swellable material. The anchor may comprise a polymerizable moiety. The anchor may include, but is not limited to, vinyl or vinyl monomers such as styrene and its derivatives (e.g., divinyl benzene), acrylamide and its derivatives, butadiene, acrylonitrile, vinyl acetate, or acrylates and acrylic acid derivatives. The polymerizable moiety may be, for example, an acrylamide modified moiety that may be covalently fixed within a swellable material.

As used herein, a "nucleic acid adaptor" is a nucleic acid sequence having a binding moiety capable of attaching to a target nucleic acid and an anchor moiety capable of attaching to the swellable material. Attaching the nucleic acid adaptor to a target nucleic acid may be accomplished by hybridization or by ligation in situ. For example, DNA adaptors may be ligated to the 3' ends of the RNAs in the sample with RNA ligases, such as T4 RNA ligase, or may be attached via a chemical linker such as a reactive amine group capable of reacting with target nucleic acid. Acrylamide modified oligonucleotide primers may be covalently fixed within a swellable material such as a polyacrylate gel. As used herein, the term "acrylamide modified" in reference to an oligonucleotide means that the oligonucleotide has an acrylamide moiety attached to the 5' end of the molecule.

As used herein, a "small molecule linker" is a small molecule having a binding moiety capable of attaching to a target nucleic acid and an anchor moiety capable of attaching to the swellable material. Attaching the small molecule linker to the target nucleic acid may be accomplished by hybridization or by a chemical reactive group capable of covalently binding the target nucleic acid. For example, Label-IT® Amine (MirusBio) is a small molecule with alkylating group that primarily reacts to the N7 of guanine, thereby allowing covalent binding of RNA and DNA. The small molecule linker may be, for example, acrylamide modified and therefore may be covalently fixed within a swellable material. As used herein, the term "acrylamide modified" in reference to a small molecule linker means that the small molecule linker has an acrylamide moiety.

As used herein, the term "attach" or "attached" refers to both covalent interactions and noncovalent interactions. In certain embodiments of the invention, covalent attachment may be used, but generally all that is required is that the bi-functional linker remain attached to the target nucleic acid under conditions for nucleic acid amplification and/or sequencing. Oligonucleotide adaptors may be attached such that a 3' end is available for enzymatic extension and at least a portion of the sequence is capable of hybridizing to a complementary sequence. Attachment can occur via hybridization to the target nucleic acid, in which case the attached oligonucleotide may be in the 3'-5' orientation. Alternatively, attachment can occur by means other than base-pairing hybridization, such as the covalent attachment set forth above. The term "attach" may be used interchangeably herein with the terms, "anchor(ed)", affix(ed), link(ed) and immobilize(d).

As used herein, the term "swellable material" generally refers to a material that expands when contacted with a liquid, such as water or other solvent. Preferably, the swellable material uniformly expands in 3 dimensions, i.e., isotropically. Additionally or alternatively, the material is transparent such that, upon expansion, light can pass through the sample. The swellable material may be a swellable polymer or hydrogel. The swellable material may be formed in situ from precursors thereof. One or more polymerizable materials, such as monomers or oligomers can be used. For example, such as monomers may be selected from the group consisting of water soluble groups containing a polymerizable ethylenically unsaturated group. Monomers or oligomers can comprise one or more substituted or unsubstituted methacrylates, acrylates, acrylamides, methacrylamides, vinylalcohols, vinylamines, allylamines, allylalcohols, including divinylic crosslinkers thereof (e.g., N,N-alkylene bisacrylamides). Precursors can also comprise polymerization initiators and crosslinkers. The precursors of a swellable material may comprise at least one polyelectrolyte monomer and a covalent crosslinker.

The swellable material may be formed in situ by chemically crosslinking water soluble oligomers or polymers. Thus, the invention envisions adding precursors of the swellable material to the sample and rendering the precursors swellable in situ. The sample may be permeated (such as, perfusing, infusing, soaking, adding or other intermixing) with the precursors of the swellable material, wherein the sample is saturated with precursors of the swellable material, which flow between and around biomolecules throughout the specimen. Polymerizing and/or crosslinking the monomers or precursors is initiated to form the swellable material or polymer in situ. In this manner the biological sample is embedded in the swellable material.

Following permeating the specimen, the swellable polymer precursors are polymerized, i.e., covalently or physically crosslinked, to form a polymer network. The polymer network is formed within and throughout the specimen. In this manner, the biological specimen is saturated with the swellable material, which flow between and around biomolecules throughout the specimen.

Polymerization may be by any method including, but not limited to, thermal crosslinking, chemical crosslinking, physical crosslinking, ionic crosslinking, photo-crosslinking, irradiative crosslinking (e.g., x-ray, electron beam), and the like, and may be selected based on the type of hydrogel used and knowledge in the art. In one embodiment, the polymer is a hydrogel. Once polymerized, a polymer-embedded biological specimen is formed.

The swellable polymer may be a polyacrylate or polyacrylamide and copolymers or crosslinked copolymers thereof. For example, if the biological sample is to be embedded in sodium polyacrylate, a solution comprising the monomers sodium acrylate and acrylamide, and a crosslinker selected from N,N-methylenebisacrylamide (BIS), N,N'-(1,2-Dihydroxythylene)bisacrylamide), and (DHEBA) N,N'-Bis(acryloyl)cystamine (BAC), are perfused throughout the sample.

The swellable material may be a hydrogel. The hydrogel may be a polyelectrolyte hydrogel. The polyelectrolyte may be a polyacrylate.

The fixed, expandable biological sample may be expanded. Expanding the sample may be accomplished by adding an aqueous solvent or liquid to cause the sample-swellable material complex to swell, thereby physically expanding the complex.

The biological sample may be expanded prior to or after the incubation step, ligation step or amplification step. In other words, the steps expanding the biological sample can be independently performed before or after any of the other steps.

The biological sample can be expanded prior to or after the incubation step, ligation step or amplification step. In other words, the steps expanding the biological sample can be independently performed before or after steps (a), (b), (c), (d), and (e). It is understood that steps (a)-(e) are performed in order. In view of the flexibility in the order of the performing each step, the article "a" is used to describe the biological sample in each step to ensure that, in each instance, the biological sample is not necessarily the product produced by the preceding step. For example, the product of step (a) can be the result of incubating a biological sample as directly obtained from a subject with a pair of polynucleotides. Alternatively, the product of step (a) can be the result of incubating a previously fixed biological sample with a pair of polynucleotides.

In one embodiment, the expandable biological sample can be expanded. The biological sample can be fixed and/or expanded prior to or after the incubation step, ligation step or amplification step. In other words, the steps of fixing (a) and expanding (b) the biological sample can be independently performed before or after steps (c), (d), (e), (f), (g) and (h). It is understood that the fixing step (a) are performed before the expanding step (b) and steps (c)-(f) are also performed in order. In view of the flexibility in the order of the performing each step, the article "a" is used to describe the biological sample in each step to ensure that, in each instance, the biological sample is not necessarily the product produced by the preceding step. For example, the product of step (c) can be the result of incubating a biological sample as directly obtained from a subject with a pair of polynucleotides. Alternatively, the product of step (c) can be the result of incubating a biological sample produced by step (a) and/or step (b) with a pair of polynucleotides.

The enlarged sample may be re-embedded in a non-swellable material. "Re-embedding" comprises permeating (such as, perfusing, infusing, soaking, adding or other intermixing) the sample with the non-swellable material, preferably by adding precursors thereof. Alternatively or additionally, embedding the sample in a non-swellable material comprises permeating one or more monomers or other precursors throughout the sample and polymerizing and/or crosslinking the monomers or precursors to form the non-swellable material or polymer. In this manner the first enlarged sample, for example, is embedded in the non-swellable material. Embedding the expanded sample in a non-swellable material prevents conformational changes during sequencing despite salt concentration variation. The non-swellable material can be charge-neutral hydrogels. For example, it can be polyacrylamide hydrogel, composed of acrylamide monomers, bisacrylamide crosslinker, ammonium persulfate (APS) initiator and tetramethylethylenediamine (TEMED) accelerator.

The fixed biological sample may be subjected to passivation. As used herein the term "passivation" refers to the process for rendering the sample less reactive with the components contained within the fixative such as by functionalizing the fixative with chemical reagents to neutralize charges within. For example, the carboxylic groups of acrylate, which may be used in the swellable gel, can inhibit downstream enzymatic reactions. Treating the swellable gel composed of acrylate with 1-Ethyl-3-(3-dimethylaminopropyl)carbodiimide (EDC) and N-Hydroxysuccinimide (NHS) allows primary amines to covalently bind the carboxylic groups to form charge neutral amides and passivate the swellable gel.

The expandable biological sample, can, optionally, be treated with a detergent prior to being contacted with the precursors of the swellable material. The use of a detergent can improve the wettability of the sample or disrupt the sample to allow the precursors of the swellable monomer to permeate throughout sample.

The sample is attached or crosslinked to the swellable material before expansion. This may be accomplished, for example, by crosslinking the anchor with the swellable material, such as during or after the polymerization, i.e., in situ formation of the swellable material.

After the sample has been anchored to the swellable material, the sample is, optionally, subjected to a disruption of the endogenous biological molecules leaving the target nucleic acids with a small molecule linker or nucleic acid adapter intact and anchored to the swellable material. In this way, the mechanical properties of the sample-swellable material complex are rendered more spatially uniform, allowing isotropic expansion with minimal artifacts.

As used herein, the "disruption of the endogenous physical structure of the sample" or the term "disruption of the endogenous biological molecules" of the biological sample generally refers to the mechanical, physical, chemical, biochemical or, preferably, enzymatic digestion, disruption or break up of the sample so that it will not resist expansion. A protease enzyme may be used to homogenize the sample-swellable material complex. The disruption should not impact the structure of the swellable material but disrupt the structure of the sample. Thus, the sample disruption should be substantially inert to the swellable material. The degree of digestion can be sufficient to compromise the integrity of the mechanical structure of the sample or it can be complete to the extent that the sample-swellable material complex is rendered substantially free of the sample. The disruption of the physical structure of the sample may be protein digestion of the proteins contained in the biological sample.

The sample-swellable material complex may then be isoptropically expanded. Expanding the sample may be accomplished by adding a solvent or liquid to the complex, which is then absorbed by the swellable material and causes swelling. Where the swellable material is water swellable, an aqueous solution can be used.

The biological sample may be labeled or tagged with a detectable label. Typically, the label or tag will bind chemically (e.g., covalently, hydrogen bonding or ionic bonding) to the sample, or a component thereof. The detectable label can be selective for a specific target (e.g., a biomarker or class of molecule), as can be accomplished with an antibody or other target specific binder. The detectable label preferably comprises a visible component, as is typical of a dye or fluorescent molecule; however, any signaling means used by the label is also contemplated. A fluorescently labeled biological sample, for example, is a biological sample labeled through techniques such as, but not limited to, immunofluorescence, immunohistochemical or immunocytochemical staining to assist in analysis. Thus, the detectable label may be chemically attached to the biological sample, or a targeted component thereof. The detectable label may be an antibody and/or fluorescent dye wherein the antibody and/or fluorescent dye further comprises a physical, biological, or chemical anchor or moiety that attaches or crosslinks the sample to the composition, hydrogel or other swellable material. The detectable label may be attached to the bi-functional linker. The detectable label may be attached to the nucleic acid adaptor or the small molecule linker. The labeled sample may furthermore include more than one label. For example, each label can have a particular or distinguishable fluorescent property, e.g., distinguishable excitation and emission wavelengths. Further, each label can have a different target specific binder that is selective for a specific and distinguishable target in, or component of the sample.

The term "polynucleotide" includes DNA, RNA or part DNA and part RNA. The polynucleotides when used in a ligation reaction with an RNA target (or target RNA) are preferably single stranded and may be partially or wholly complementary to at least a portion of the RNA target (or target RNA). Additionally, a polynucleotide can be native to the sample (for example, present in the sample at the time the sample is obtained from the original organism). Alternatively, a polynucleotide can be artificial or synthetic, such as when the polynucleotide is added to the sample to cause hybridization to a target RNA. The term "polynucleotide" is intended to include polynucleotides comprising naturally occurring nucleotides and/or non-naturally occurring nucleotides. Non-naturally occurring nucleotides can include chemical modifications of natural nucleotides. In this case, it is preferred that the synthetic polynucleotides can hybridize to the target RNA.

The term "a pair of polynucleotides" refers to two oligonucleotides that have complementary sequences to the target RNA. Each polynucleotide of the pair is also referred to herein as a "target-complementary polynucleotide". In one embodiment, the pair of polynucleotides comprise two independent, linear polynucleotides that are complementary to non-overlapping and proximal sequences of the target RNA. The 5' end of one of the polynucleotides and the 3' end of the other polynucleotide are brought into juxtaposition by hybridization to a target sequence. This juxtaposition allows the two polynucleotides to be covalently joined by the action of a ligase.

In one embodiment, a pair of polynucleotides can refer to a single pair of polynucleotides. In another embodiment, a pair of polynucleotides can refer to a library of polynucleotide pairs, wherein each independent pair comprises two polynucleotides complementary to non-overlapping and proximal sequences of a target RNA. For example, a library of polynucleotides pairs can comprise 2 or more polynucleotide pairs, 10 or more polynucleotide pairs, 100 or more polynucleotide pairs, 1000 or more polynucleotide pairs, 10,000 or more polynucleotide pairs, or more than 20,000 polynucleotide pairs, including any number in between. It is important to note that a polynucleotide pair preferably consists of two polynucleotides. However, it is possible that each "pair" have three or more polynucleotides complementary to non-overlapping and proximal sequences of a target RNA.

The term "complementary to non-overlapping and proximal sequences of the target RNA" refers to a pair of polynucleotides where one polynucleotide is complementary to a sequence of the target RNA and the other polynucleotide(s) is/are complementary to a different sequence of the target RNA, wherein the distance between the ends of the two polynucleotides, also referred to as the "ligation junction," as measured by nucleobases, is preferably less than about 20 nucleobases. In one embodiment, the polynucleotides are from 0 to about 20 nucleobases apart (e.g., the ligation junction is less than 20 nucleobases). In one embodiment, the polynucleotides are from 0 to about 15 nucleobases apart (e.g., the ligation junction is less than 15 nucleobases). In one embodiment, the polynucleotides are from 0 to about 10 nucleobases apart (e.g., the ligation junction is less than 10 nucleobases). In one embodiment, the polynucleotides are from 0 to about 5 nucleobases apart (e.g., the ligation junction is less than 5 nucleobases). In one embodiment, the ligation junction is selected form the group consisting of 0, 1, 2, 3, 4, 5, 6, 7, 8, 9, 10, 11, 12, 13, 14, 15, 16, 17, 18, 19, or 20 nucleobases. In one embodiment, the ligation junction is 0 nucleobase. In a preferred embodiment, the ligation junction is zero and the 5' end of one polynucleotide abuts the 3' end of the other polynucleotide.

The nature of pair of polynucleotides and stringent requirements for ligation make them especially useful for in situ hybridization and detection of a target RNA. In situ hybridization is a technique where the polynucleotides are hybridized with the target RNA sequence that is to be detected, wherein this sequence is present at its original place (in-situ), i.e., within the cell or tissue, thereby aiding in localizing the target sequence.

The polynucleotides can comprise additional sequences that can be used for amplification, for example, primer binding sites, and/or identification via DNA tag or barcode.

Each polynucleotide of the pair of polynucleotides is independently from about 8 to about 100 nucleotides in length. In one embodiment, each polynucleotide is independently from about 8 to about 40 nucleotides long. In one embodiment, each polynucleotide is independently from about 10 to about 100 nucleotides long. In one embodiment, each polynucleotide is independently from about 10 to about 40 nucleotides long. In one embodiment, each polynucleotide is independently from about 8 to about 25 nucleotides long. In one embodiment, each polynucleotide is independently from about 10 to about 25 nucleotides long. In one embodiment, each polynucleotide is independently from about 15 to about 23 nucleotides long. In one embodiment, each polynucleotide is about 16 nucleotides long. In one embodiment, each polynucleotide is the same number of nucleotides in length.

In one embodiment, the pair of polynucleotides are part of a single, linear oligonucleotide comprising the two polynucleotides complementary to non-overlapping and proximal sequences of the target RNA connected by a polynucleotide linker, wherein one of the target-complementary polynucleotides is at the 5' end of the oligonucleotide and the other target-complementary polynucleotide is at the 3' end of the oligonucleotide.

The 5' end and the 3' end of the oligonucleotide are brought into juxtaposition by hybridization to a target sequence, forming a circle above the target. This juxtaposition allows the ends of the oligonucleotide to be covalently joined by the action of a ligase.

The nature of pair of polynucleotides and stringent requirements for ligation make them especially useful for in situ hybridization and detection of a target RNA. In situ hybridization is a technique where the polynucleotides are hybridized with the target RNA sequence that is to be detected, wherein this sequence is present at its original place (in-situ) within the cell or tissue, thereby aiding in localizing the target sequence.

The oligonucleotide can comprise additional sequences that can be used for amplification, for example, primer binding sites, and/or identification via DNA tag or barcode. In one embodiment, these additional sequences are located within the linker sequence.

Each target-complementary polynucleotide of the oligonucleotide is independently from about 8 to about 100 nucleotides in length. In one embodiment, each polynucleotide is independently from about 8 to about 40 nucleotides long. In one embodiment, each polynucleotide is independently from about 10 to about 100 nucleotides long. In one embodiment, each polynucleotide is independently from about 10 to about 40 nucleotides long. In one embodiment, each polynucleotide is independently from about 8 to about 25 nucleotides long. In one embodiment, each polynucleotide is independently from about 10 to about 25 nucleotides long. In one embodiment, each polynucleotide is independently from about 15 to about 23 nucleotides long. In one embodiment, each polynucleotide is about 16 nucleotides long. In one embodiment, each polynucleotide is the same number of nucleotides in length.

The polynucleotide linker can be of any length sufficient to allow both of the target-complementary polynucleotide ends of the oligonucleotide to bind the target sequence. In this respect, the polynucleotide linker is at least as long as the length of the target-complementary polynucleotide ends combined. For example, if the target-complementary polynucleotides are each 8 nucleotides in length then the polynucleotide linker comprises at least 16 nucleotides. In one embodiment, the polynucleotide linker is from about 16 to about 200 nucleotides long. In one embodiment, the polynucleotide linker is from about 20 to about 100 nucleotides long. In one embodiment, the polynucleotide linker is from about 20 to about 60 nucleotides long. In one embodiment, the polynucleotide linker is from about 20 to about 50 nucleotides long. In one embodiment, the polynucleotide linker is about 42 nucleotides long.

The pair of polynucleotides, when exposed to a biological sample, will bind with the target RNA, thereby forming a hybrid. The biological sample is exposed to a ligase and upon recognition of and hybridization to the target RNA by the 5' end of one of the target-complementary polynucleotides and the 3' end of the other target-complementary polynucleotide the polynucleotide pairs are ligated to each other through the action of a ligase. The pair of polynucleotides can hybridize the target with a high index of specificity due to the fact that two arms are required to bind target segments independently, which is subsequently ligated.

Where the pair of polynucleotides comprise two independent linear polynucleotides complementary to adjacent sequences within the target RNA (i.e., the ligation junction is 0), the polynucleotides hybridize to the target RNA and are ligated by a ligase into a single linear polynucleotide.

The length of the ligated polynucleotide is equal to the length of the two target-complementary polynucleotides.

Where the pair of polynucleotides comprise two independent linear polynucleotides complementary to proximal but non-adjacent sequences within the target RNA (i.e., the ligation junction gap is about 1-20 nucleotides in length), upon hybridization of the polynucleotides to the target RNA the gap between the polynucleotides must be filled prior ligation by the ligase. The gap can be filled by any method known to one skilled in the art, for example, but not limited to, using a DNA polymerase such as a Reverse transcriptase and free nucleotides to fill the gap. Once the gap is filled, the ends of the polynucleotides are ligated by a ligase into a single linear polynucleotide. The length of the ligated polynucleotide is equal to the length of the two target-complementary polynucleotides plus the number of nucleotides required to fill the gap.

Where the pair of polynucleotides are part of a single, linear oligonucleotide comprising the two target-complementary polynucleotides connected by a polynucleotide linker, both ends of the oligonucleotide hybridize with the target DNA sequence facing each other, forming a circular structure. In the presence of a DNA ligase, the ends of the oligonucleotide are ligated, thus, a circular closed structure is formed above the target RNA. Where the pair of polynucleotides are complementary to adjacent sequences within the target RNA (i.e., the ligation junction is 0), the polynucleotides hybridize to the target RNA and are ligated by a ligase into a single, circular oligonucleotide. The length of the ligated polynucleotide is equal to the length of the oligonucleotide.

Where the pair of polynucleotides are complementary to proximal but non-adjacent sequences within the target RNA (i.e., the ligation junction gap is about 1-20 nucleotides in length), upon hybridization of the polynucleotides to the target RNA the gap between the polynucleotides must be filled prior ligation by the ligase. The gap can be filled by any method known to one skilled in the art, for example, but not limited to, using a DNA polymerase such as a Reverse transcriptase and free nucleotides to fill the gap. Once the gap is filled, the ends of the polynucleotides are ligated by a ligase into a single, circular oligonucleotide. The length of the ligated oligonucleotide is equal to the length of the oligonucleotides plus the number of nucleotides required to fill the gap.

The nature of the pair of polynucleotides and stringent requirements for ligation are especially useful for in-situ hybridization. In-situ hybridization is a technique where the probe is hybridized with the target DNA or RNA sequence that is to be detected, wherein the sequence is present at its original place (in-situ), i.e., within the cell, tissue sections, thereby aiding in localizing the target sequence at its original place.

Ligation can be accomplished either enzymatically or chemically. "Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide.

A variety of template-driven ligation reactions are described in the following references: Whitely et al., U.S. Pat. No. 4,883,750; Letsinger et al., U.S. Pat. No. 5,476,930; Fung et al., U.S. Pat. No. 5,593,826; Kool, U.S. Pat. No. 5,426,180; Landegren et al., U.S. Pat. No. 5,871,921; Xu and Kool (1999) Nucl. Acids Res. 27:875; Higgins et al., Meth. in Enzymol. (1979) 68:50; Engler et al. (1982) The Enzymes, 15:3 (1982); and Namsaraev, U.S. Patent Pub. 2004/0110213.

Chemical ligation methods are disclosed in Ferris et al., Nucleosides & Nucleotides, 8: 407-414 (1989) and Shabarova et al., Nucleic Acids research, 19: 4247-4251 (1991). Enzymatic ligation utilizes a ligase. Many ligases are known to those of skill in the art as referenced in Lehman, Science, 186: 790-797 (1974); Engler et al., DNA ligases, pages 3-30 in Boyer, editor, The Enzymes, Vol. 15B (Academic Press, New York, 1982); and the like. Exemplary ligases include SplintR ligase, T4 DNA ligase, T7 DNA ligase, E. coli DNA ligase, Taq ligase, Pfu ligase and the like. Certain protocols for using ligases are disclosed by the manufacturer and also in Sambrook, Molecular Cloning: A Laboratory manual, 2.sup.nd Edition (Cold Spring Harbor Laboratory, New York, 1989); barany, PCR Methods and Applications, 1:5-16 (1991); Marsh et al., Strategies, 5:73-76 (1992). In one embodiment, the ligase may be derived from algal viruses such as the Chlorella virus, for example, PBCV-1 ligase, also known as SplintR ligase, as described US Patent Publication No. 2014/0179539, incorporated herein by reference in its entirety.

The expression "amplification" or "amplifying" refers to a process by which extra or multiple copies of a particular polynucleotide are formed. The term "amplification product" refers to the nucleic acids, which are produced from the amplifying process as defined herein.

Amplification includes methods generally known to one skilled in the art such as, but not limited to, PCR, ligation amplification (or ligase chain reaction, LCR), real time (rtPCR) or quantitative PCR (qPCR), rolling circle amplification (RCA), and other amplification methods. These methods are generally known. See, e.g., U.S. Pat. Nos. 4,683,195 and 4,683,202 and Innis et al., "PCR protocols: a guide to method and applications" Academic Press, Incorporated (1990) (for PCR); and Wu et al. (1989) Genomics 4:560-569 (for LCR). In one embodiment, the ligation product is amplified using PCR. In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified. In one embodiment, the ligation product is amplified using qPCR. Quantitative polymerase chain reaction is used to simultaneously detect a specific DNA sequence in a sample and determine the actual copy number of this sequence relative to a standard. In one embodiment, the ligation product is amplified using rtPCR. In real-time PCR, the DNA copy number can be established after each cycle of amplification. By using a fluorescent reporter in the reaction, it is possible to measure DNA generation.

In one embodiment, the ligation product is amplified using RCA. Rolling circle amplification describes a process of unidirectional nucleic acid replication that can rapidly synthesize multiple copies of circular molecules of DNA or RNA.

Through suitable design of a probe sequence outside the target-complementary polynucleotides, detection may be performed through various methods. One example is loop-mediated isothermal amplification (LAMP), wherein probes are designed to form LAMP target structures upon ligation (Notomi, et al., *Nucleic Acids Res.*, 28(12): e63 (2000)). Presence of target RNA is then detected via LAMP amplification, enabling advantages such as isothermal reaction conditions, rapid detection, and implementation in field or point-of-care diagnostics. Upon successful ligation, detection of amplification of target nucleic acid via may be performed with traditional qPCR dyes and probes as described above, or with additional methodologies: turbidity detection of precipitated magnesium pyrophosphate (Mori, et. al., *Biochem. Biophys. Res. Commun.*, 289:150-154 (2001)); colorimetric detection using metal-sensitive indicators (Tomita, et. al., *Nat. Protocols*, 3(5):877-82 (2008); Goto, et al., *BioTechniques*, 46(3):167-71 (2009)); bioluminescence through pyrophosphate conversion (Gandelman, et al., *PLoS One*, 5:e14155 (2010)); or detection via change in pH due to amplification in weakly-buffered conditions (Pourmand, et. al., *PNAS*, 103(17):6466-70 (2006); U.S. Pat. No. 7,888,015; and U.S. patent application Ser. No. 13/799,995.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

A Sequencing can be carried out by any method known in the art including, but not limited to, sequencing by hybridization, sequencing by ligation or sequencing by synthesis. Sequencing by ligation includes, but is not limited to, fluorescent in situ sequencing (FISSEQ). Sequencing by synthesis includes, but is not limited to, reversible terminator chemistry (i.e. Illumina SBS).

EXAMPLES

While a preferred embodiment is disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention, which is not to be limited except by the claims that follow.

A fixed sample was pre-hybridize by incubating with wash buffer (WA-10, 10% formamide, 2×SSC) for 20 minutes at room temperature. Polynucleotide pairs were prepared by diluting in wash A-10 at the desired concentration and then vortexed to mix. The polynucleotide pairs were diluted to between 2-20 nM per probe. The sample was incubated with the polynucleotide pairs for more than 6 hours at 37 C. The sample was washed twice with excess volume (e.g., 500 ul for 24-well plates) of WA-10 at 37 C for 30 mins per wash. The sample was then washed once with excess volume 1× PBS at 37 C for 30 mins.

Following hybridization, the sample was preincubated with SplintR ligase (1×) buffer for 20 mins. The sample was then incubated with the following for more than 6 hours at room temperature (RT):

| Component | Amount (µl) | Final concentration |
|---|---|---|
| Nuclease-free H2O | 90 | |
| 10x Buffer | 20 | 1x |
| SplintR ligase | 10 | 1.25 units/uL |
| Total | 200 | |

The sample was then washed twice with PBS for 15 min per wash.

Amplification of ligated product(s) was performed by rolling circle amplification (RCA). The sample was incubated with the RCA primer at 37 C for 2 hr:

| Component | Amount (µl) | Final concentration |
|---|---|---|
| Nuclease-free H2O | 139 | |
| Formamide, 100% | 40 | 20% |
| SSC buffer, 20x | 20 | 2x |
| RCA primer, 100 µM | 1 | 0.5 µM |
| Total | 200 | |

The sample was then washed once with A-10 for 30 min and then with PBS for 30 min. The following was used to perform RCA:

| Component | Amount (µl) | Final concentration |
|---|---|---|
| Nuclease-free H2O | 176 | |
| Phi29 buffer, 10x | 20 | 1x |
| dNTP, 25 mM | 2 | 250 µM |
| Phi29 DNA polymerase | 2 | 1 U/µl |
| Total | 200 | |

If the ligation products, or components thereof (e.g., barcode(s)) are to be sequenced, AA-dUTP is added at 40 uM. Without sequencing, do not add the AA-duTP. The sample was then washed briefly with 1× PBS for 2×.

Detection of rolonies, or RCA colonies, was performed using Rolony Hybridization with the following for 1 hour at RT:

| Component | Amount (µl) | Final concentration |
|---|---|---|
| Nuclease-free H2O | 140 | |
| Formamide, 100% | 20 | 10% |
| SSC buffer, 20x | 40 | 4x |
| Rolonies hybridization probe, 100 µM | 0.2 | 0.1 µM |
| Total | 200 | |

The sample was then washed with 1× PBS, 3 times 15 min,

Following detection, the amplicons can be sequenced by any method known in the art.

In Situ Sequencing

Incorporation mix ("IMT") was extracted from the cartridges of, respectively, a MiSeq Reagent Kit v3 and a NextSeq 500/550 Reagent Kit v2, aliquoted, and frozen. Four template oligonucleotides (see Table 2.1, each with a unique base downstream of a primer binding site) were individually annealed with primer at a concentration of 45 uM in 1× Annealing Buffer (1× TE pH 7.5, 50 mM NaCl) in a thermal cycler. The annealing involved a 3 minute hold at 95 degrees followed by a −0.1° C. ramp to 25 C. 500 pmol of each of the template-primer duplexes were separately diluted 1:10 into MiSeq and NextSeq IMT. The dilutions were heated at 65° C. for 5 minutes, and then eluted in 20 uL of water using a DNA oligonucleotide clean and concentrate kit (Zymo). The elutant from each reaction was added to a well of a 384-well glass bottom plate, and the absorption and emission spectra were measured using a spectrophotometer.

TABLE 2.1

Oligonucleotides used in spectral characterization

| Oligonucleotide | Sequence |
| --- | --- |
| Template (A) | GTACTGAACTGTCTCTTATACACATCTGACGCTGCCGACGA (SEQ ID NO: 1) |
| Template (T) | GTACTGTTCTGTCTCTTATACACATCTGACGCTGCCGACGA (SEQ ID NO: 2) |
| Template (C) | GTACTGCCCTGTCTCTTATACACATCTGACGCTGCCGACGA (SEQ ID NO: 3) |
| Template (G) | GTACTGGGCTGTCTCTTATACACATCTGACGCTGCCGACGA (SEQ ID NO: 4) |
| Primer | TCGTCGGCAGCGTCAGATGTGTATAAGAGACAG (SEQ ID NO: 5) |

Base-specific DNA template-primer duplexes were prepared and, following a single base of synthesis using MiSeq or NextSeq kit-specific fluorescent incorporation mix, the templates were physically isolated from unreacted dyes, and their emission and absorption spectra were measured via spectrophotometry.

The MiSeq absorption spectra is presented in FIG. 2. There are distinct absorbance maxima for dTTP at 580 nm, dATP at 650 nm, and dCTP at 700 nm. dGTP has two absorbance maxima: a larger one at 530 nm and a smaller one at 640 nm, although it should be noted that both of these maxima are small compared to the maxima for the other three fluorescent dNTPs. In order to relate the absorption maxima to emission spectra, a full spectrum measurement emission measurement was collected for each sample when excited 20-30 nm away from an absorption maximum. There are distinct emission maxima for dGTP at 550 nm, dTTP at 600 nm, dATP at 670 nm, and dCTP at 720 nm.

The NextSeq absorption spectra is presented in FIG. 2. There are distinct absorbance maxima for dTTP at 560 nm, dCTP at 650 nm. dATP has two absorbance maxima of roughly equal intensity at 530 nm and at 660 nm. dGTP has two small absorbance maxima at similar locations to dATP. A similar approach to the last section was used to measure the emission spectra of these samples. There are distinct emission maxima for dATP at 550 nm and 680 nm, dTTP at 580 nm, and dCTP at 670 nm. dGTP can be considered effectively dark when compared to the other three dyes. The results from the spectral measurements are summarized in two tables, Table 2.2 and Table 2.3.

TABLE 2.1

Summary of MiSeq spectral measurements.

| Fluorescent dNTP | Absorbance Maximum (nm) | Emission Maximum (nm) |
| --- | --- | --- |
| dGTP | 530 | 550 |
| dTTP | 580 | 600 |
| dATP | 650 | 670 |
| dCTP | 700 | 720 |

TABLE 2.2

Summary of NextSeq spectral measurements.

| Fluorescent dNTP | Absorbance Maximum (nm) | Emission Maximum (nm) |
| --- | --- | --- |
| dGTP | Effectively dark | Effectively dark |
| dTTP | 560 | 580 |
| dATP | 650 | 670 |
| dCTP | 530 and 660 | 550 and 680 |

Having obtained spectra for all colors in each of the MiSeq and NextSeq kits a biological sequence can be attributed to a sequence of colors observed under a conventional fluorescence microscope. The ability to attribute a base ("base call") to a cluster depends on both the fidelity of the sequencing chemistry as well as the properties of the lasers and filters used in a particular microscope.

FISSEQ-like in situ RNA sequencing libraries were prepared in hydrogel embedded and expanded rat neuron culture.

Incorporation mix ("IMT"), scan mix ("USM") and cleavage mix ("CMS") were extracted from the cartridges of a MiSeq Reagent Kit v3, aliquoted, and frozen. To perform the sequencing reaction, a sample of RNA sequencing library prepared hydrogel (approximately 3 microliters in volume) was washed twice with 300 uL (i.e. 100× sample volume) of PR2 buffer (supplied with MiSeq kit) for five minutes each. The sample was next immersed in 300 uL IMT, held at 4 C for 10 minutes, then held at 65 C for 30 minutes to incorporate one base of fluorescent dNTP into the library. The sample was then washed twice for 30 minutes with 300 uL of PR2 buffer and then exchanged into 300 uL of USM for imaging. Describe confocal microscope here. Following imaging, the sample was washed twice for 5 minutes with 300 uL of PR2 buffer and exchanged into 300 uL of CMS for 30 minutes at room temperature for cleavage. This process was completed five times to generate five successive image stacks of the region of interest.

To analyze the data, a maximum intensity projection was first performed for each image stack, and each projection was then separated into three images corresponding to each of the imaging channels. For each of these images, maxima coordinates were extracted using the Find Maxima process with manual noise thresholding, generating lists of maxima for each of the three channels for each of the rounds of sequencing.

Using a Python script, intensity tuples were generated from these maxima coordinates. Briefly, for each maximum in a particular channel, an intensity tuple was generated corresponding to the local intensity of that maximum in each of the three channels (rather than just the channel it was detected in), where local intensity is defined as the average of the 3×3 pixel neighborhood centered on the maximum. The local intensities for an individual channel are exponentially distributed; the three distributions were normalized to the intensity of the dimmest channel (here, the 488 nm channel) by scaling the means of the distributions. The normalized intensity tuples for each of the maxima detected in the 488 nm channel and the 560 nm channel were used to generate the crosstalk plots. Pearson's r was computed using for each plot by first aggregating the two sets of intensity tuples and then using the SciPy library of the same name. The fraction of spots passing the threshold intensity was computed as described below.

Sequencing by synthesis on an RNA sequencing library generated in situ was demonstrated. A series of five successive sequencing reactions were performed in situ using reagents extracted from reagent cartridges supplied with a commercially-available Illumina MiSeq kit. The cells were fixed and subsequently embedded in an swellable hydrogel as described herein, providing enhanced resolution and generating a quasi-in-vitro environment in which enzymatic reactions can occur. The sequencing library itself was prepared according to a method similar to FISSEQ (i.e. the nucleic acid clusters are prepared via randomly primed reverse transcription, followed by circularization and phi29-mediated rolling circle amplification).

Figure 3:
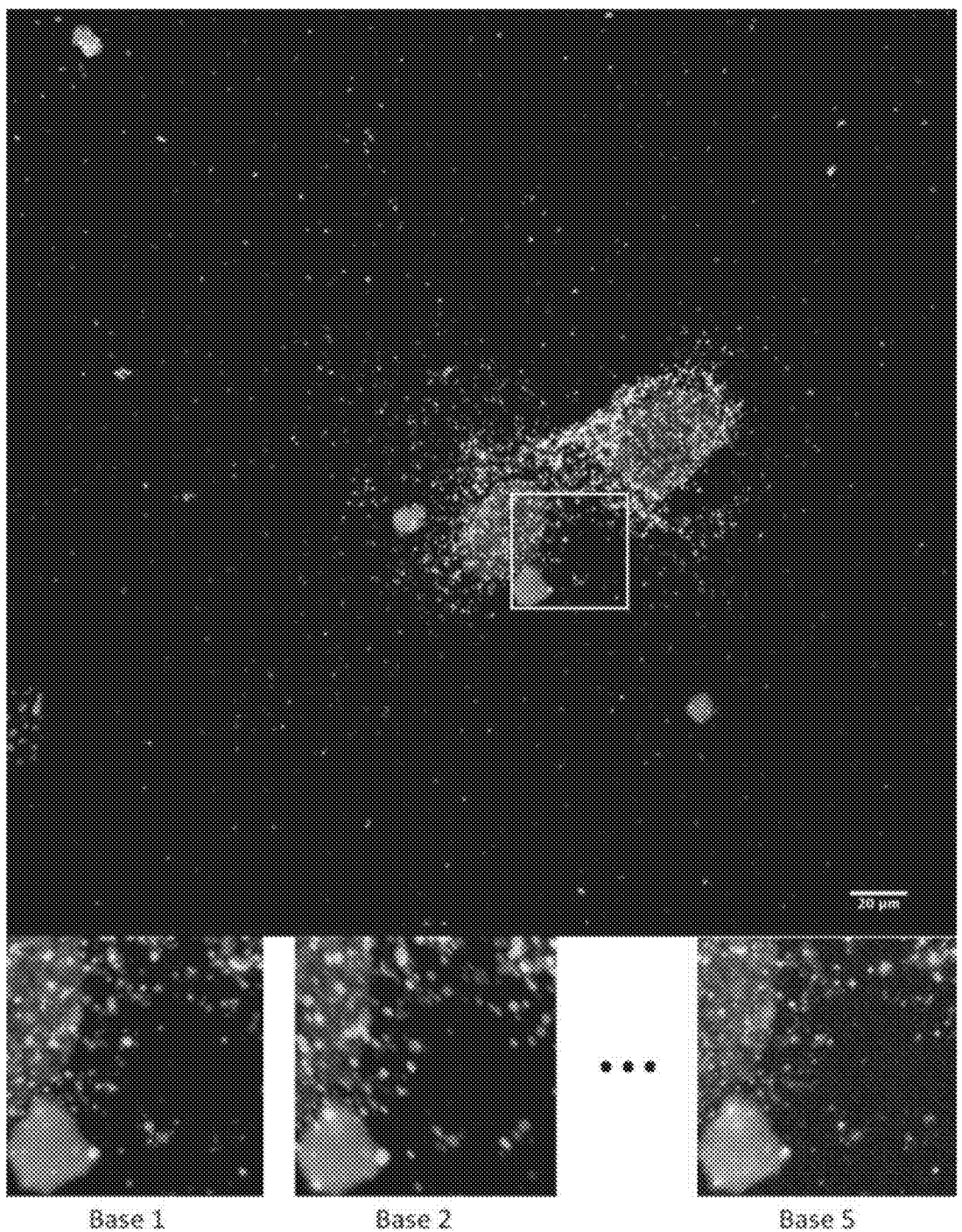
FIG. 3. Demonstration of sequencing by synthesis in situ. (a) Representative region of interest of an initial base of sequencing of an RNA sequencing library prepared in an expanded sample. (b) Multiple bases of sequencing by synthesis. Individual clusters change color from round-to-round.

A representative region of interest (ROI) from the sequenced sample, after the first base of sequencing, is shown in FIG. 3(a). Visual inspection indicates that individual clusters correspond to one particular color (they are "clonal") rather than a blend of colors ("polyclonal"). Individual clusters also change color from round-to-round, as expected; this is illustrated in FIG. 3(b).

There are four dye colors in a MiSeq kit; however, due to constraints on the lasers and filters available, all four bases were not imaged independently. The dye corresponding to G can be imaged independently using a standard 488 nm channel, and the dye corresponding to T can be imaged independently using a 560 nm channel; however, the dyes corresponding to A and C are both excited and visible using a 640 nm channel. This can be corroborated by examining the number of maxima in each channel detected for the ROI. This degeneracy introduces ambiguity in sequence reconstruction; however, the performance of the sequencing reactions themselves in situ, and in particular with round-to-round phasing, can proceed by only examining the 488 nm and 560 nm channels, since, as demonstrated, only two independent channels are required for this purpose.

Figure 4:
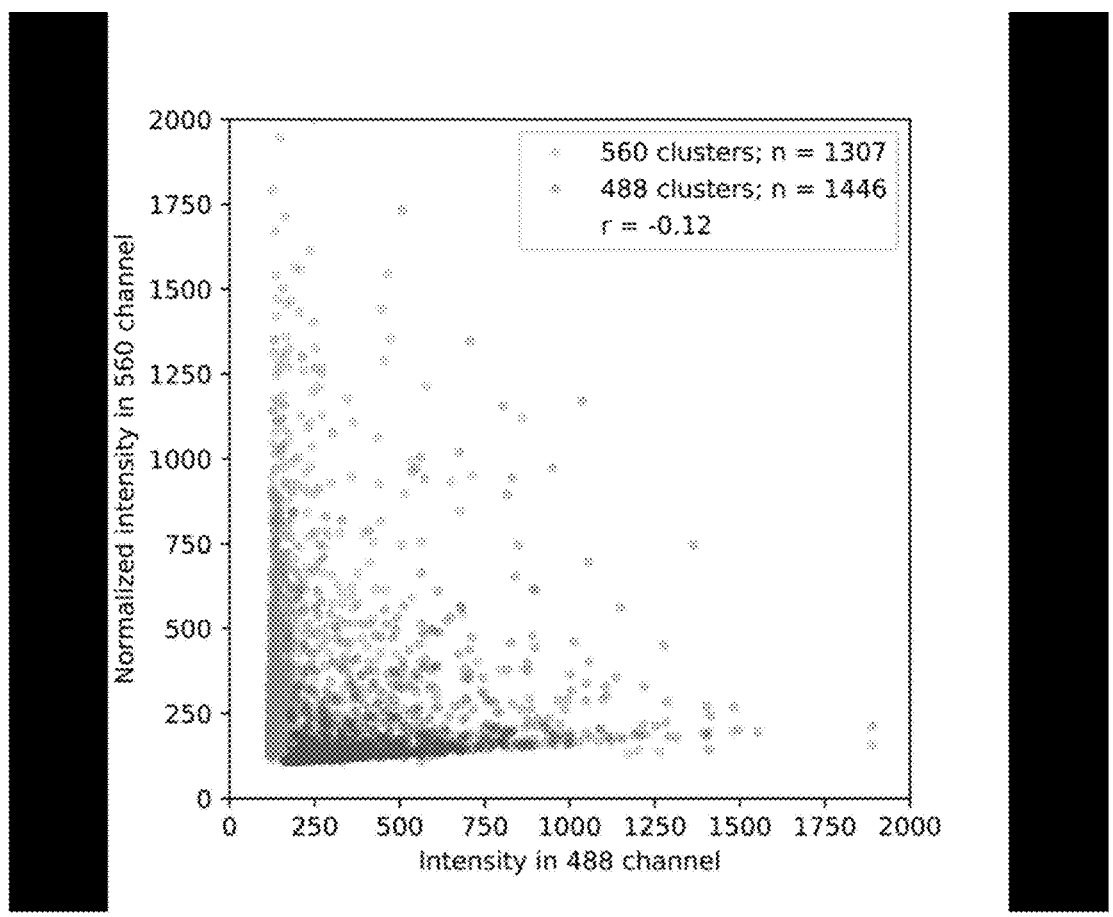
FIG. 4. Intensity crosstalk plot for the first base of sequencing for clusters detected in the 488 nm channel ("G") and the 560 nm channel ("T"). The clusters separate into two distinct, roughly orthogonal components, and the aggregate dataset shows low correlation, both indicative of highly clonal clusters.
Figure 4:
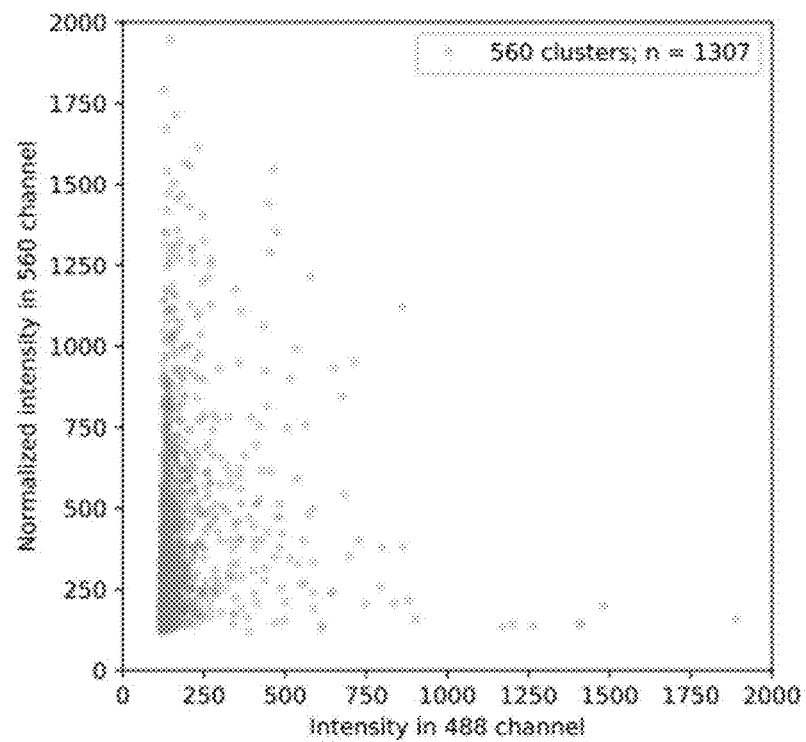
Figure 4:
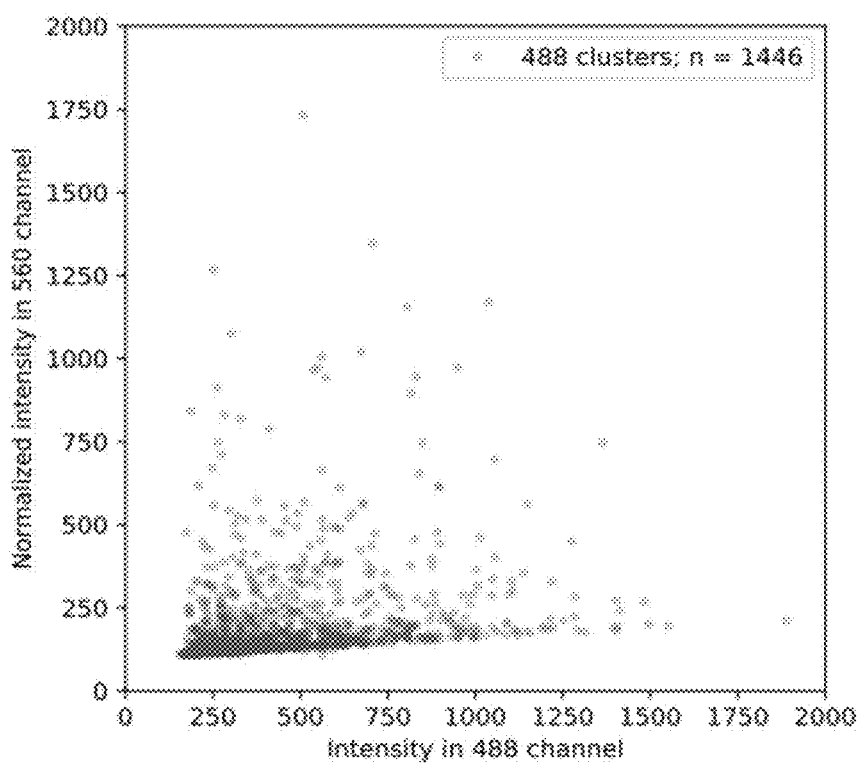

In order to quantify the phasing, the images were processed in order to generate pairs of cluster intensities; that is, for each cluster identified as a maximum in the 488 channel or the 560 channel, the intensities of that cluster in both the 488 and 560 channels were extracted. The pairs of intensities for all clusters (i.e. identified in either channel), for the first base of sequencing, are plotted in aggregate as a crosstalk plot in FIG. 4, with a color assigned to each set of clusters as a guide to the eye.

Figure 5:
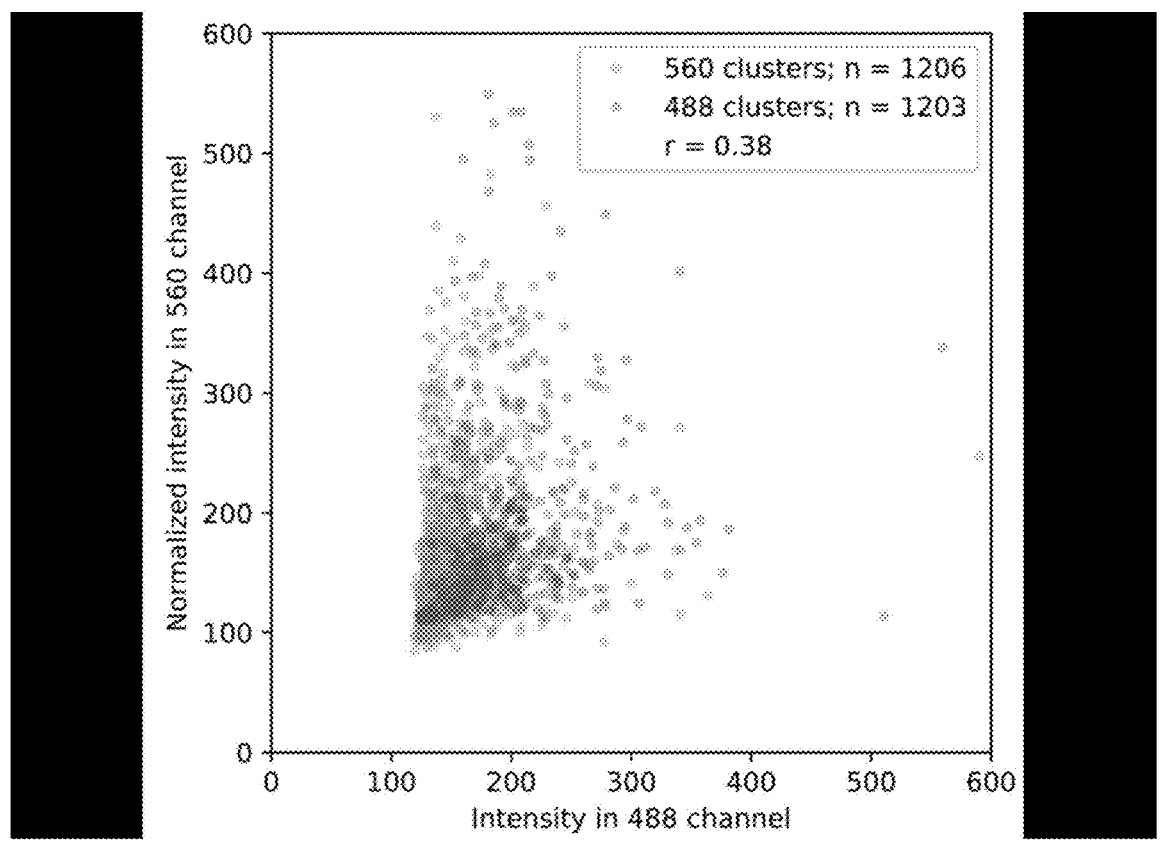
FIG. 5. Intensity crosstalk plot for the fifth base of sequencing. The clusters have become significantly dimmer and more correlated, indicating incomplete addition and an increase in polyclonality.
Figure 5:
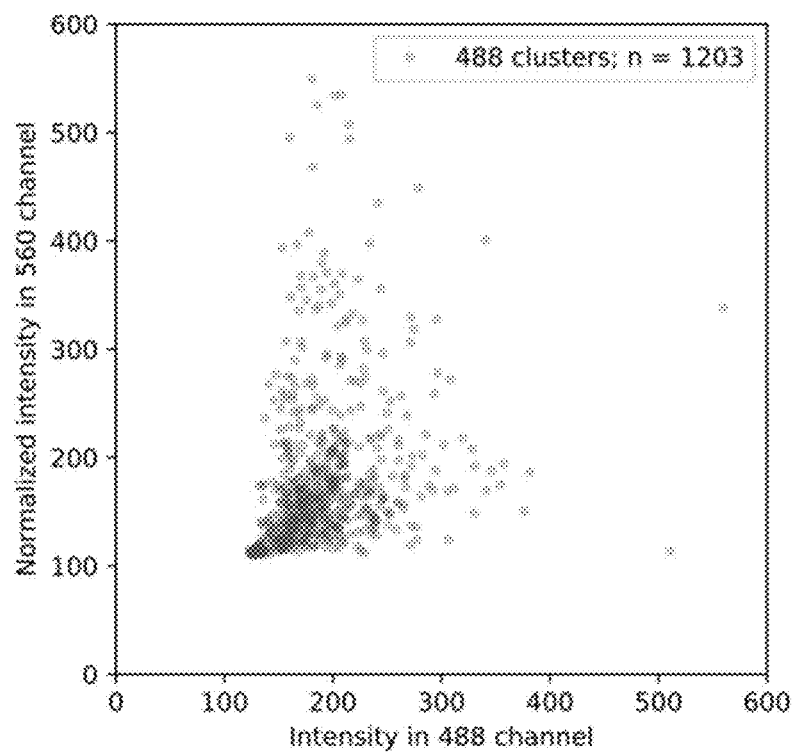
Figure 5:
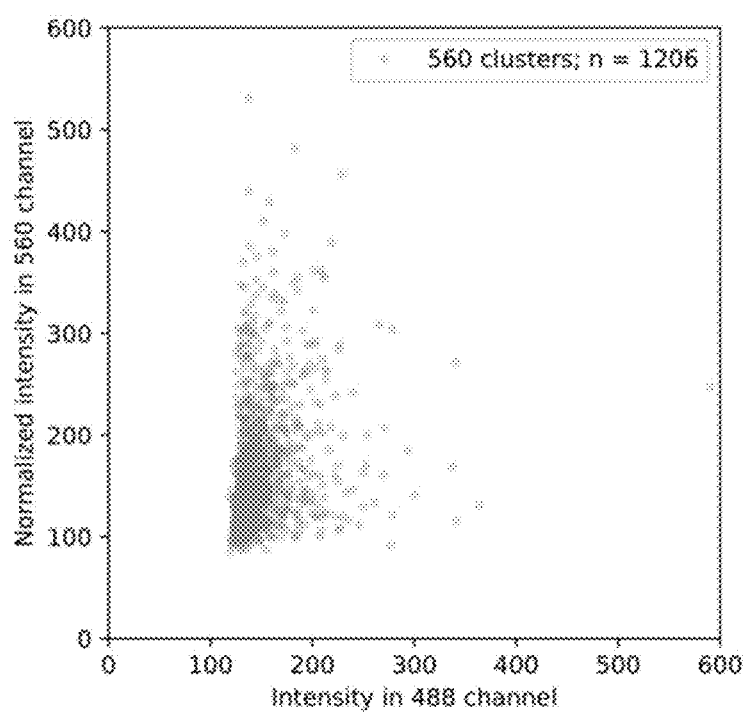

A "perfect" dataset would be composed of two perfectly orthogonal components (i.e. every dye cluster is monoclonal), however any real cluster will have some degree of crosstalk due to chemistry errors, noise, or experimental biases (i.e. excitation crosstalk). It is clear from visual inspection of FIG. 4 that there are two approximately orthogonal components corresponding to monoclonal clusters, with a smaller set of polyclonal clusters falling between the two arms of the crosstalk plot. The cluster polyclonality increases over multiple sequencing rounds: FIG. 5 plots the cluster crosstalk for the fifth round of sequencing, where the two components are highly correlated and difficult to visually distinguish.

Figure 6:
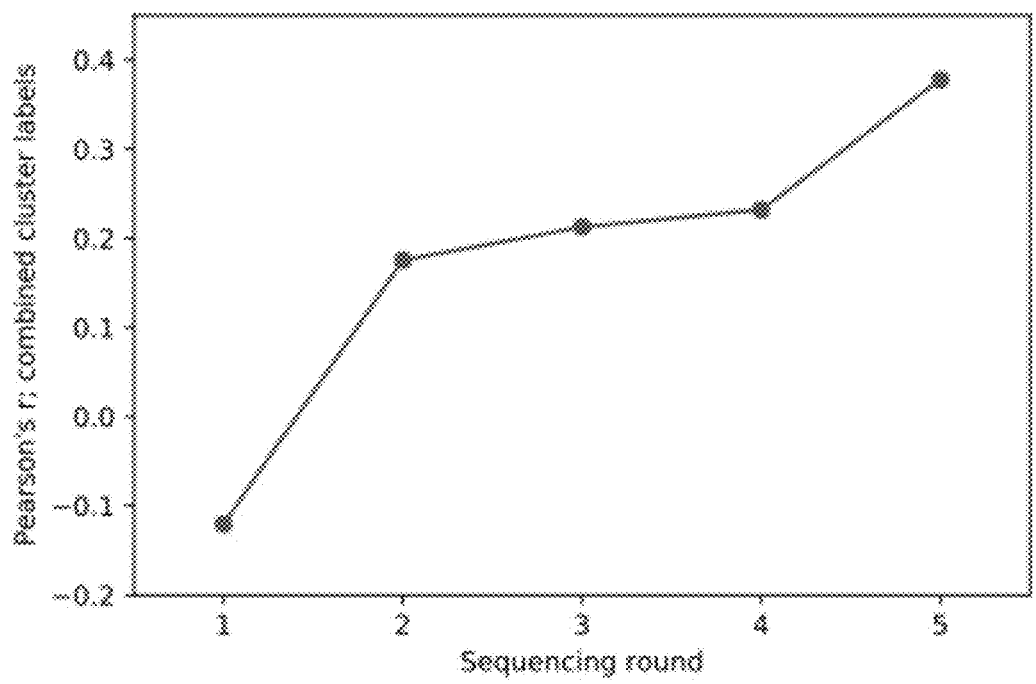
FIG. 6. Crosstalk plot correlation over multiple sequencing rounds. The correlation increases monotonically and roughly linearly, indicating a steady accumulation of chemistry errors (phasing).
Figure 6:
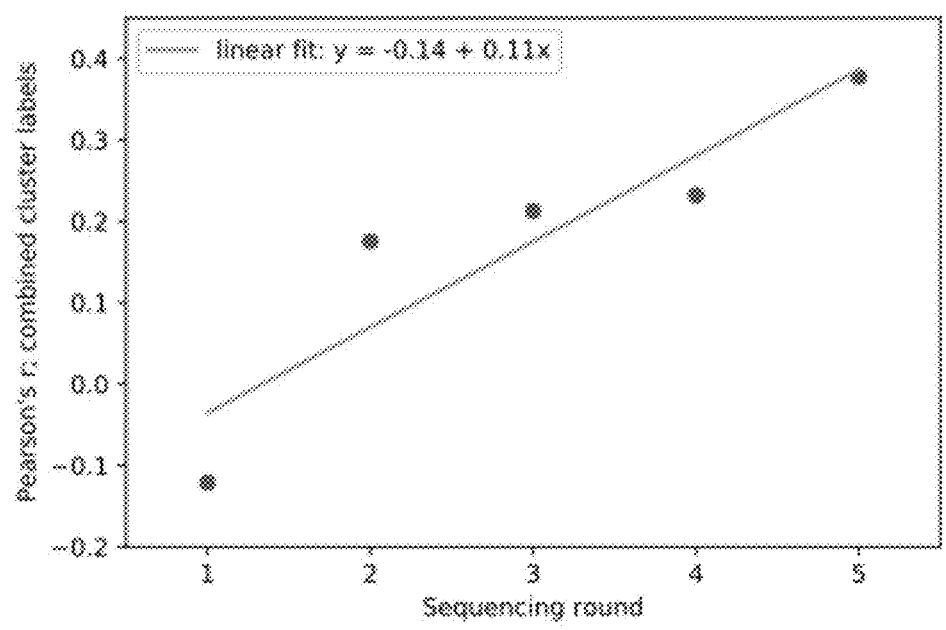

One facile method to quantify the cluster crosstalk over sequencing cycles is to compute Pearson's correlation coefficient (r) for both components in aggregate: as the two arms of the crosstalk plot become less orthogonal due to phasing, they are necessarily more correlated. As see in FIG. 6 that r increases monotonically and roughly linearly with successive rounds of sequencing.

Figure 7:
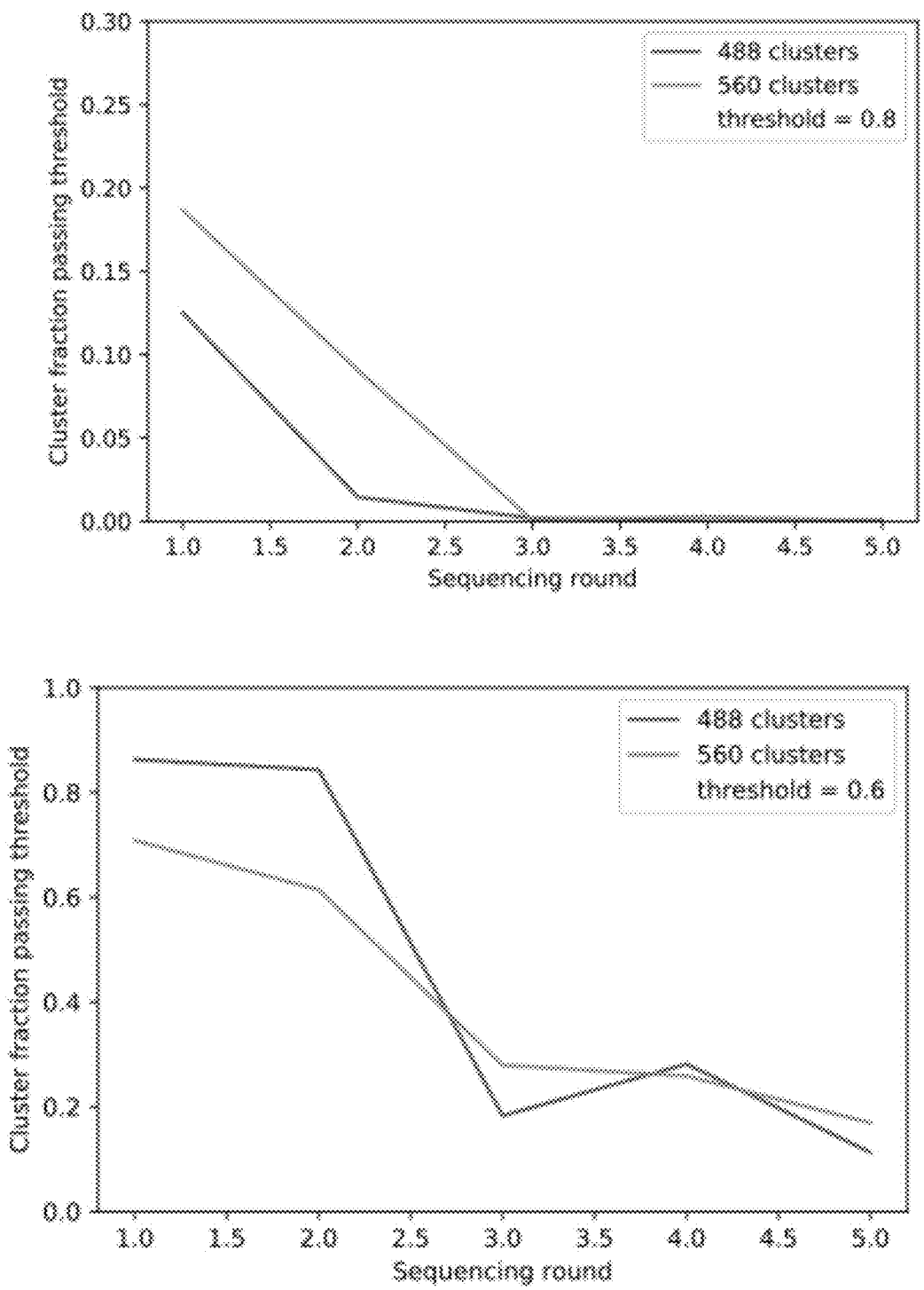
FIG. 7. Analysis of phasing on a per-cluster basis, showing the fraction of clusters that are sufficiently clonal to pass an intensity threshold (i.e. a "chastity filter").

The crosstalk correlation is useful but incomplete metric, since individual clusters may still be "callable" if one color remains dominant. To explore this possibility a second, threshold intensity based metric similar to the CHASTITY metric used in certain base calling methods was defined. A threshold intensity is defined as:

$$I_T = \frac{I_{highest\ channel}}{I_{highest\ channel} + I_{second\ highest\ channel}}$$

and compute IT for each cluster in the crosstalk plot (there are, of course, only two channels). The fraction of all clusters passing the threshold for two different representative thresholds in FIG. 7 were plotted, where a threshold of 0.6 is typical. A majority of clusters pass this threshold for the first and second rounds of sequencing, but the quality declines rapidly thereafter; this effect is even more pronounced for a threshold of 0.8.

A naive use of MiSeq reagents in this in situ context permits identification of the first few bases of a cluster, but the sequencing fidelity falls rapidly with successive rounds of sequencing. This is attributable to a high degree of round-to-round phasing, as demonstrated by the steady increase in correlation between the two intensity components of each cluster. These results suggest that optimizations increasing the yield and fidelity of the MiSeq sequencing reaction would be desirable in order to generate long, biologically meaningful reads.

Methods were performed as described above, with the sole exception of the IMT incubation step being repeated before each round of imaging.

Figure 8:
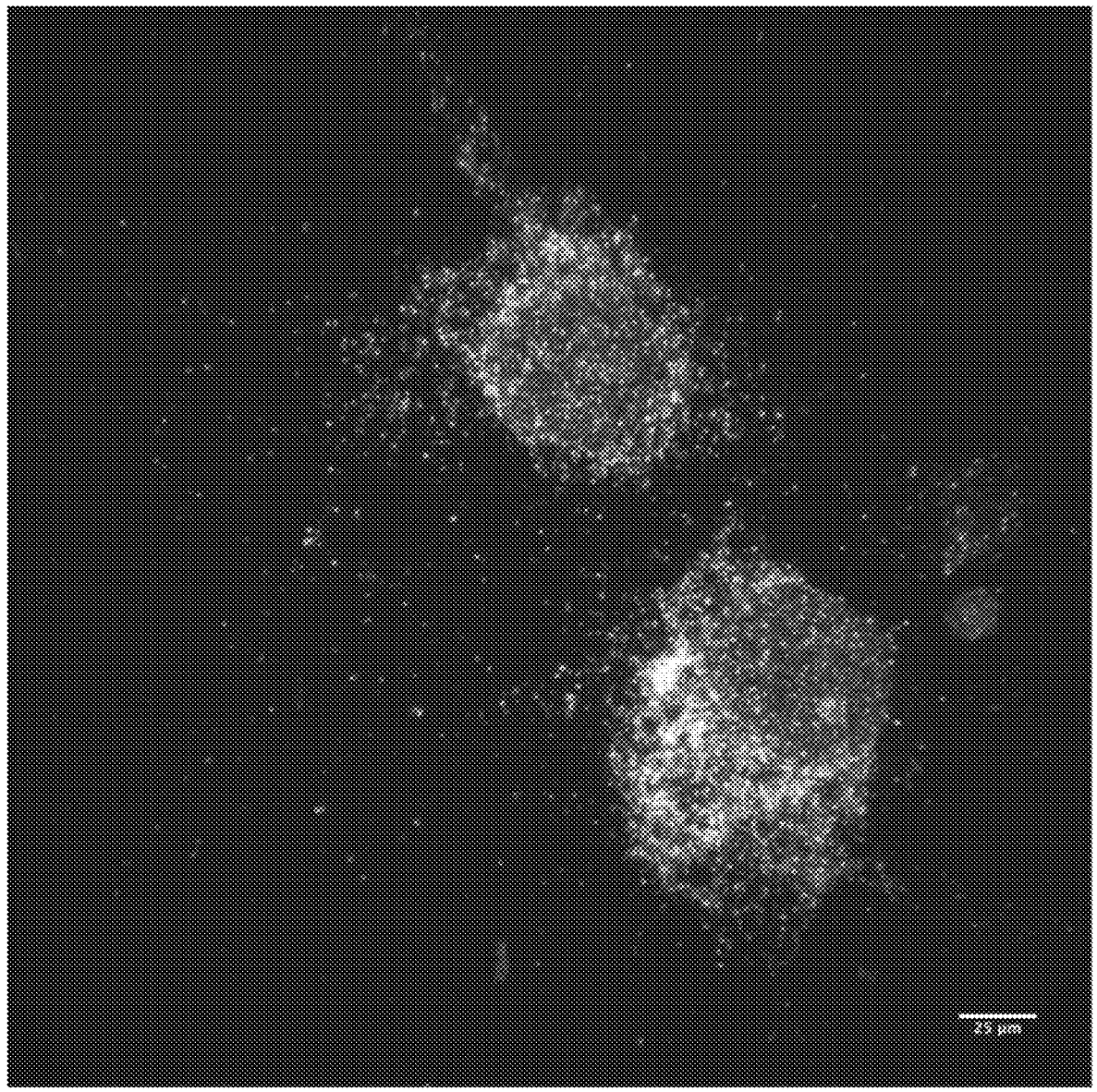
FIG. 8. Representative region of interest of an initial base of sequencing of an RNA sequencing library prepared in an expanded sample, with two rounds of synthesis before imaging.
Figure 9:
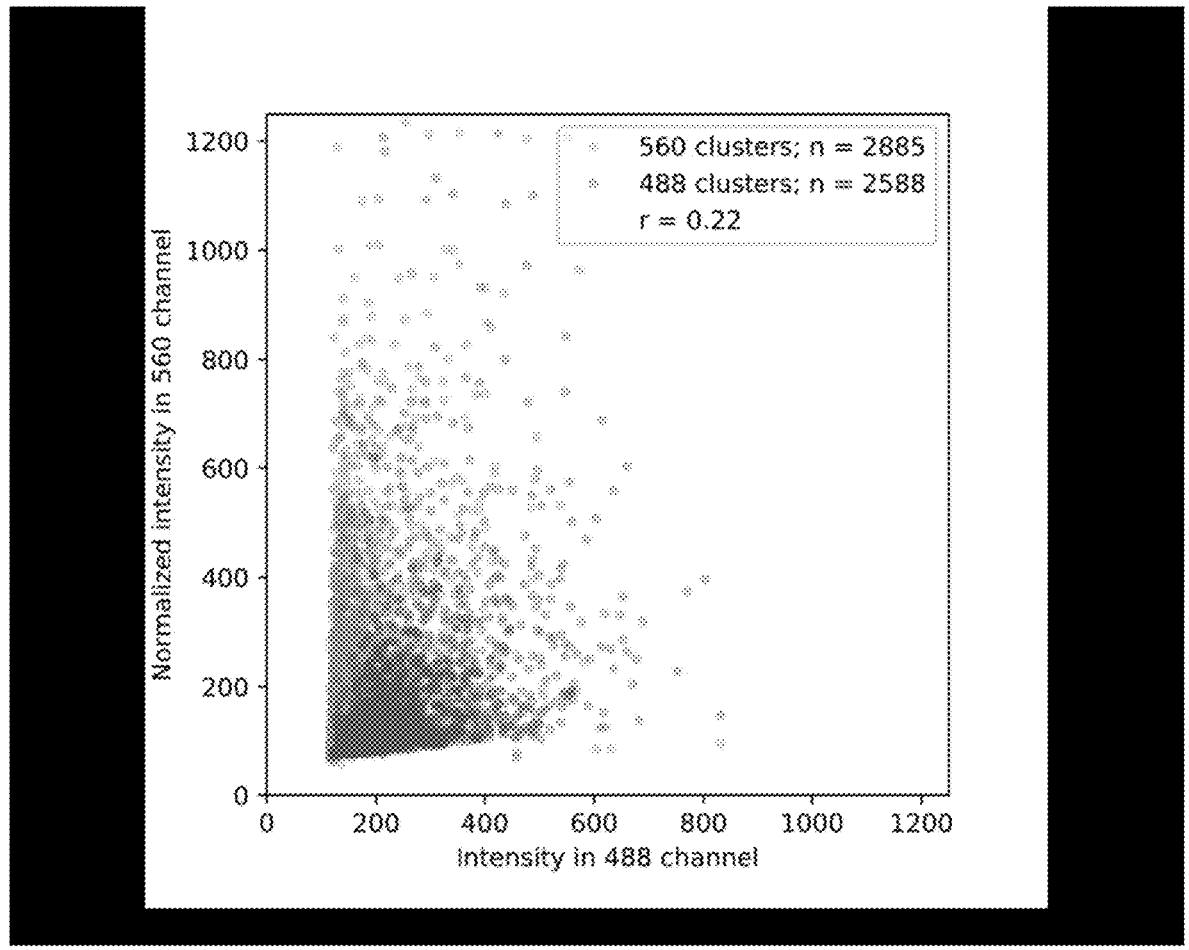
FIG. 9. Crosstalk plot for the first base of sequencing, with two rounds of synthesis before imaging. The two channels are more correlated initially than in the analogous case for one round of synthesis (see FIG. 4).
Figure 9:
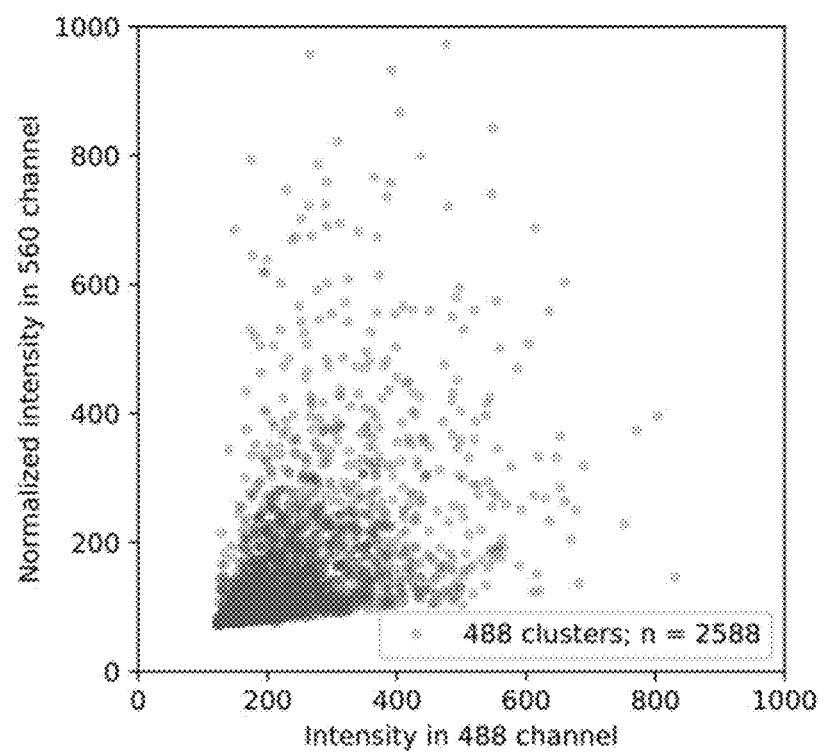
Figure 9:
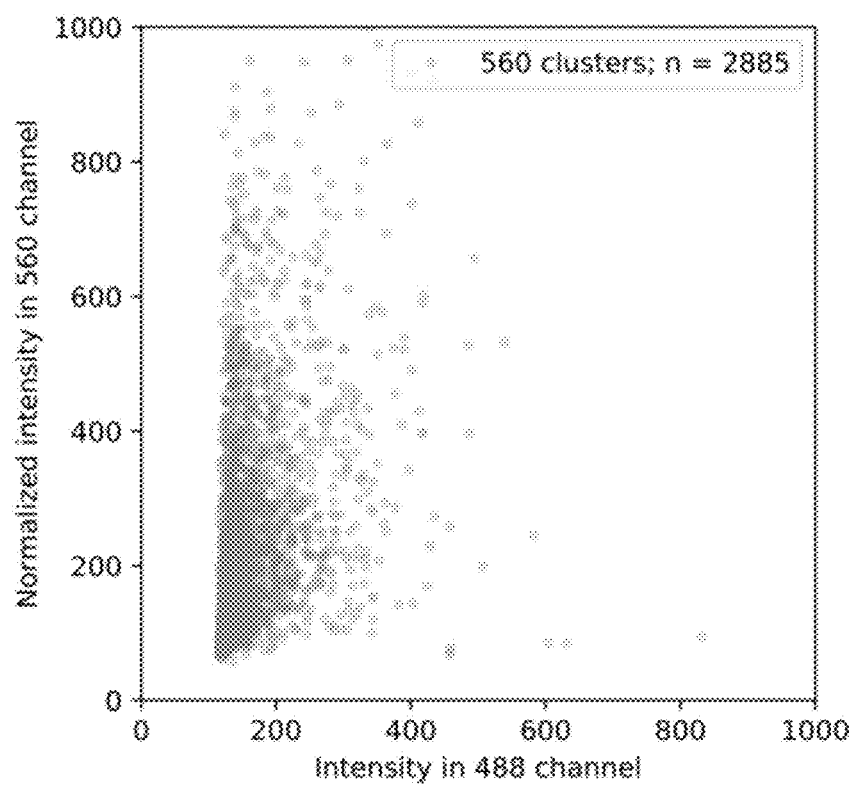
Figure 10:
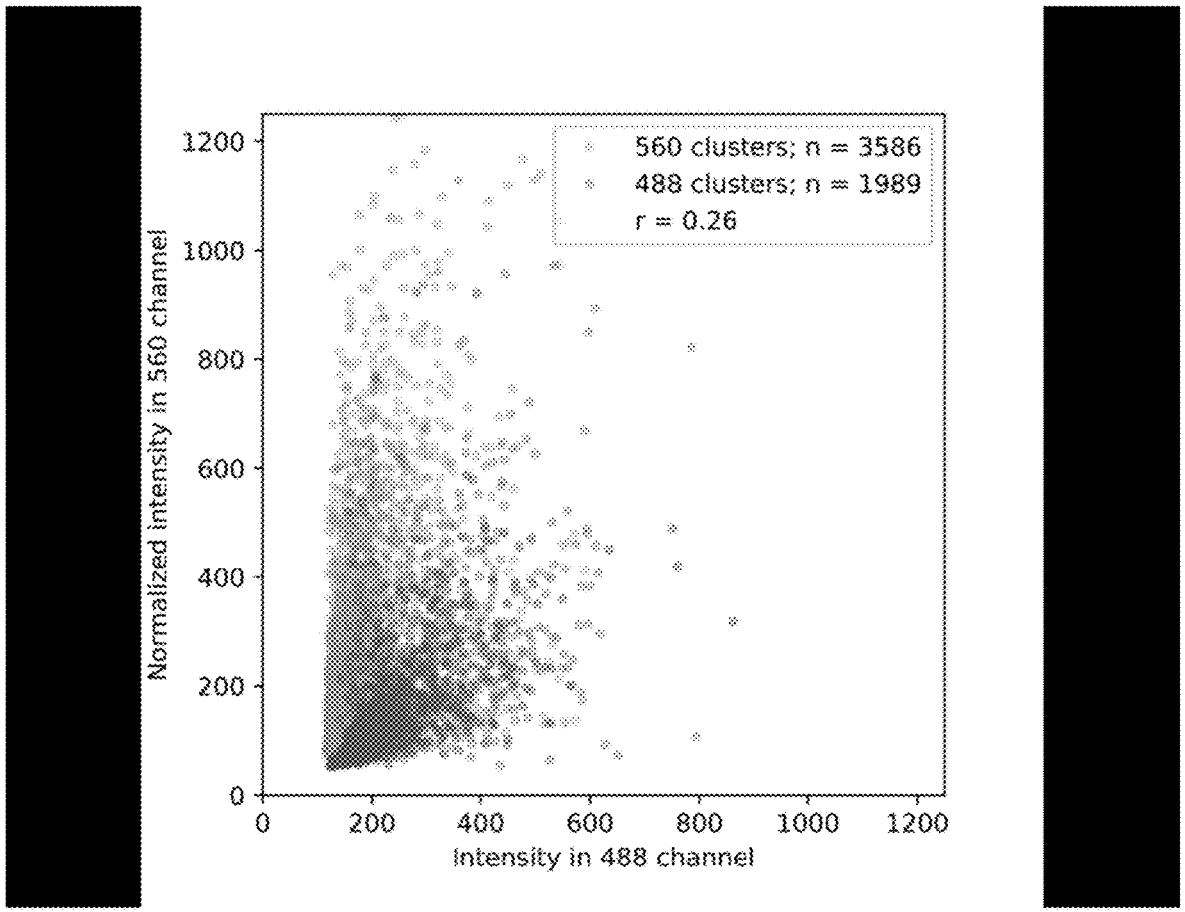
FIG. 10. Crosstalk plot for the seventh base of sequencing, with two rounds of synthesis before imaging. The two channels have not become significantly more correlated over seven cycles of sequencing.
Figure 10:
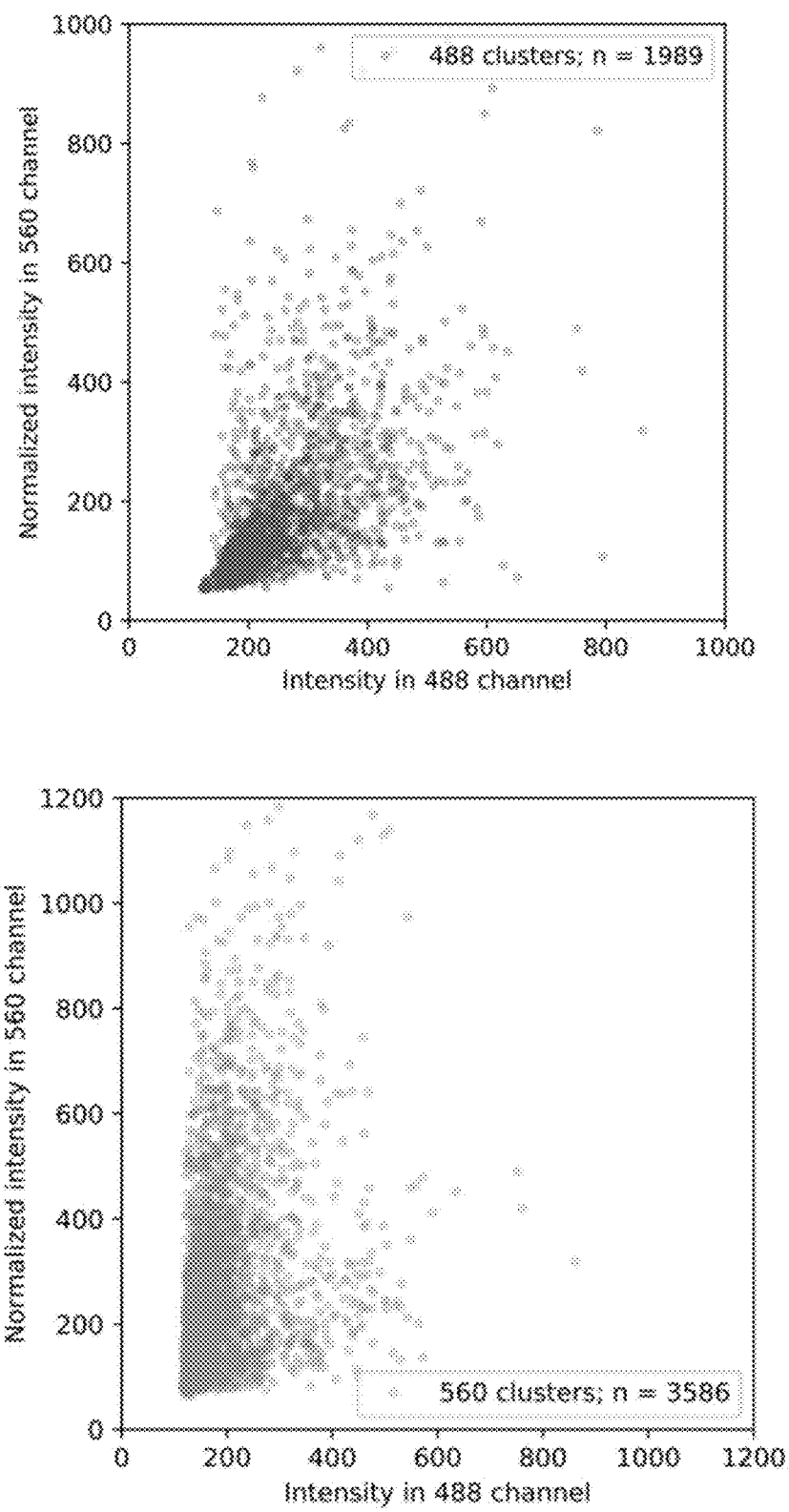
Figure 11:
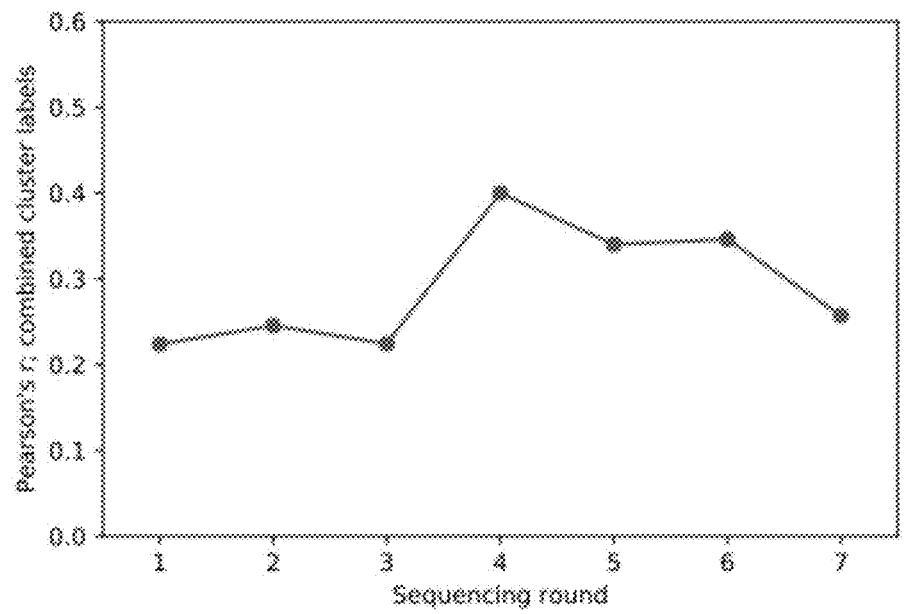
FIG. 11. Crosstalk plot correlation over multiple sequencing rounds with two rounds of synthesis.
Figure 11:
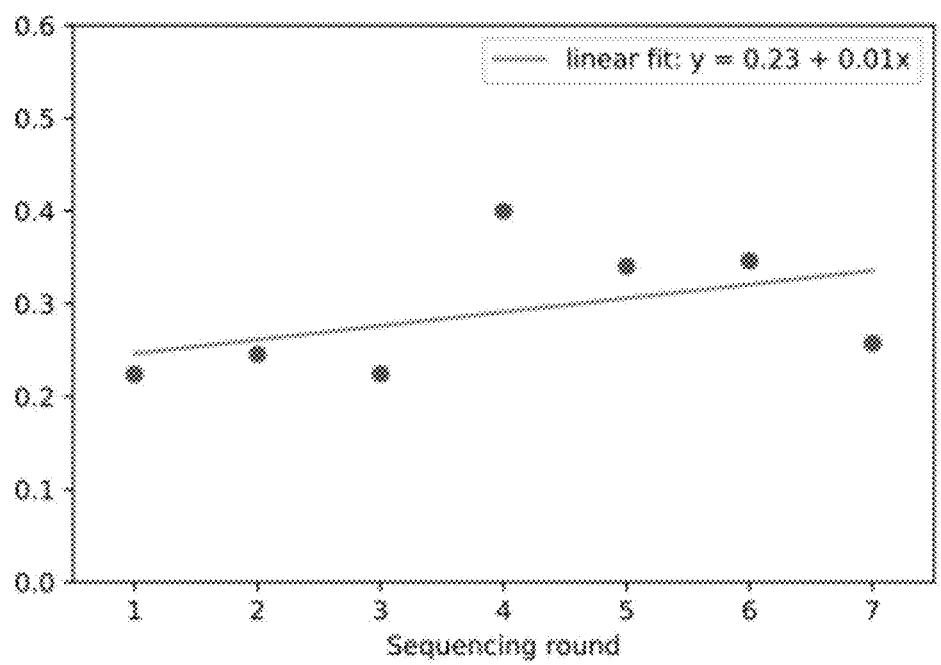
Figure 12:
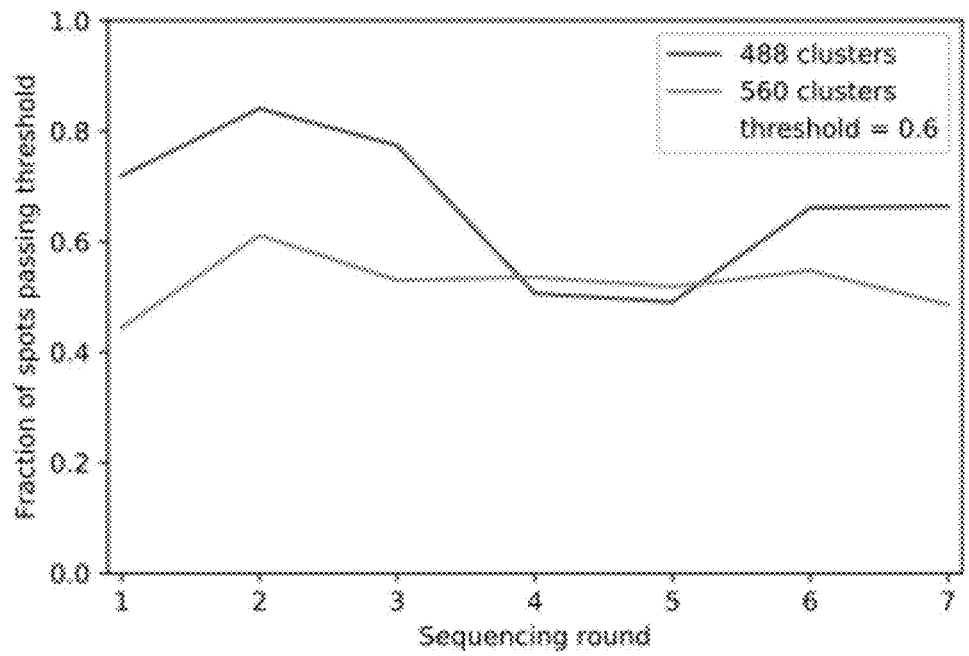
FIG. 12. Fraction of clusters passing the intensity threshold. Unlike the analogous case in FIG. 7, a significant fraction of clusters consistently pass the 0.6 threshold.
Figure 12:
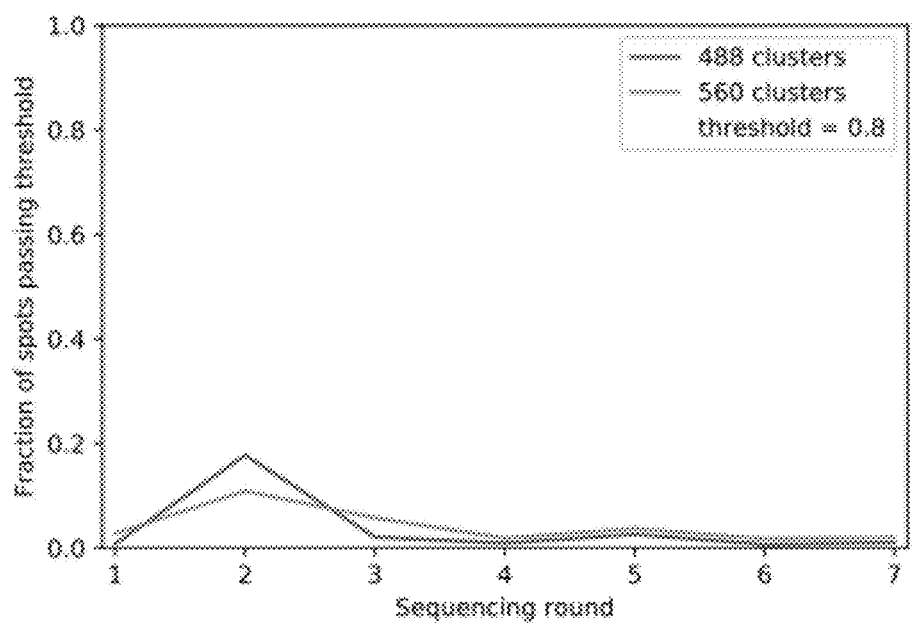
Figures 13A, 13B, 13C:
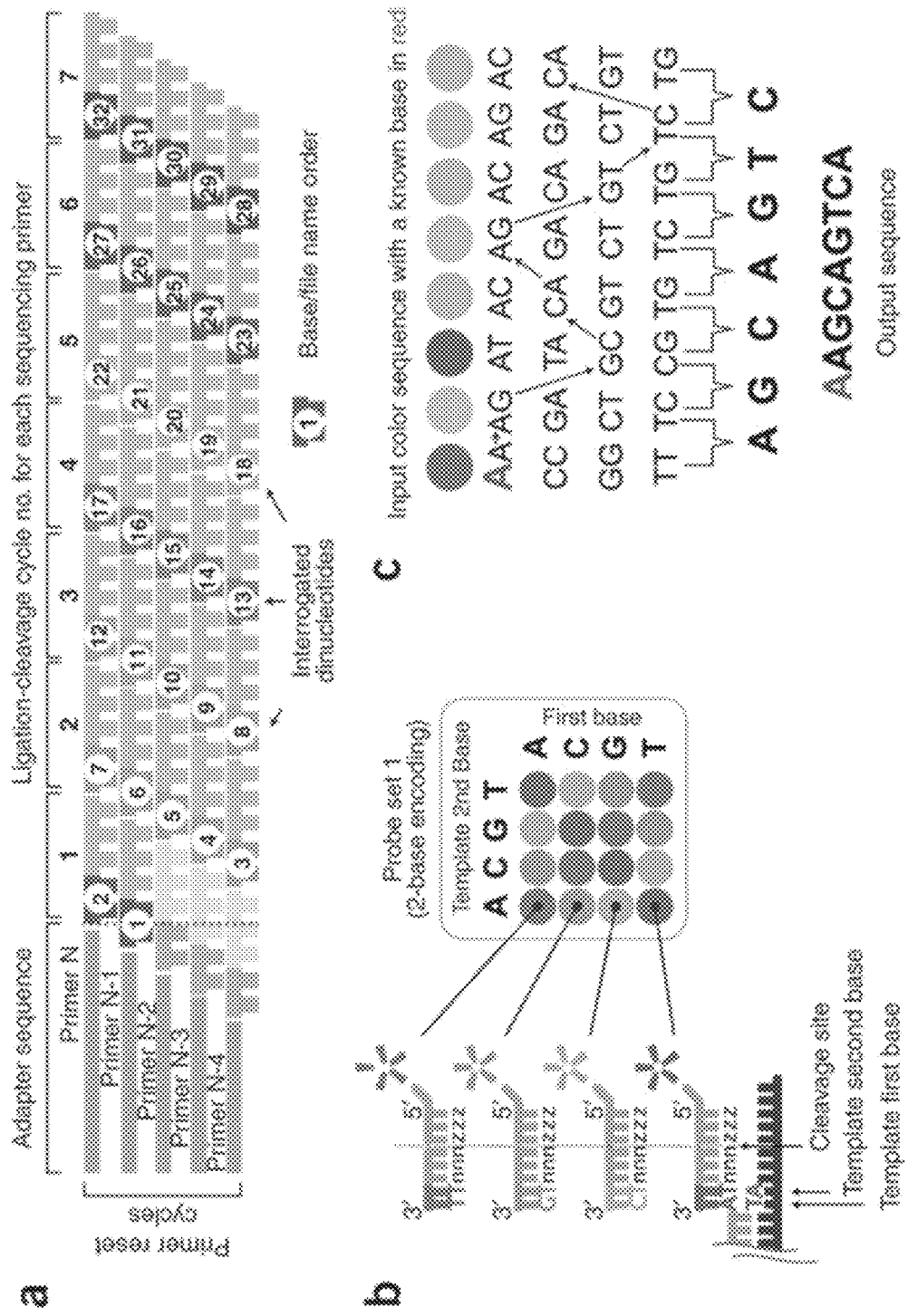
FIG. 13. Conceptual illustration of SOLiD sequencing by ligation. (a) A template strand is sequenced by successive cycles of ligation and cleavage of fluorescent dinucleotide probes. Multiple sequencing primers with different starting positions are used; each base is ultimately assayed twice. (b) Two-base encoding scheme used in SOLiD. (c) The true biological sequence can be reconstructed from a "color space" two-base encoding.
Figure 14:
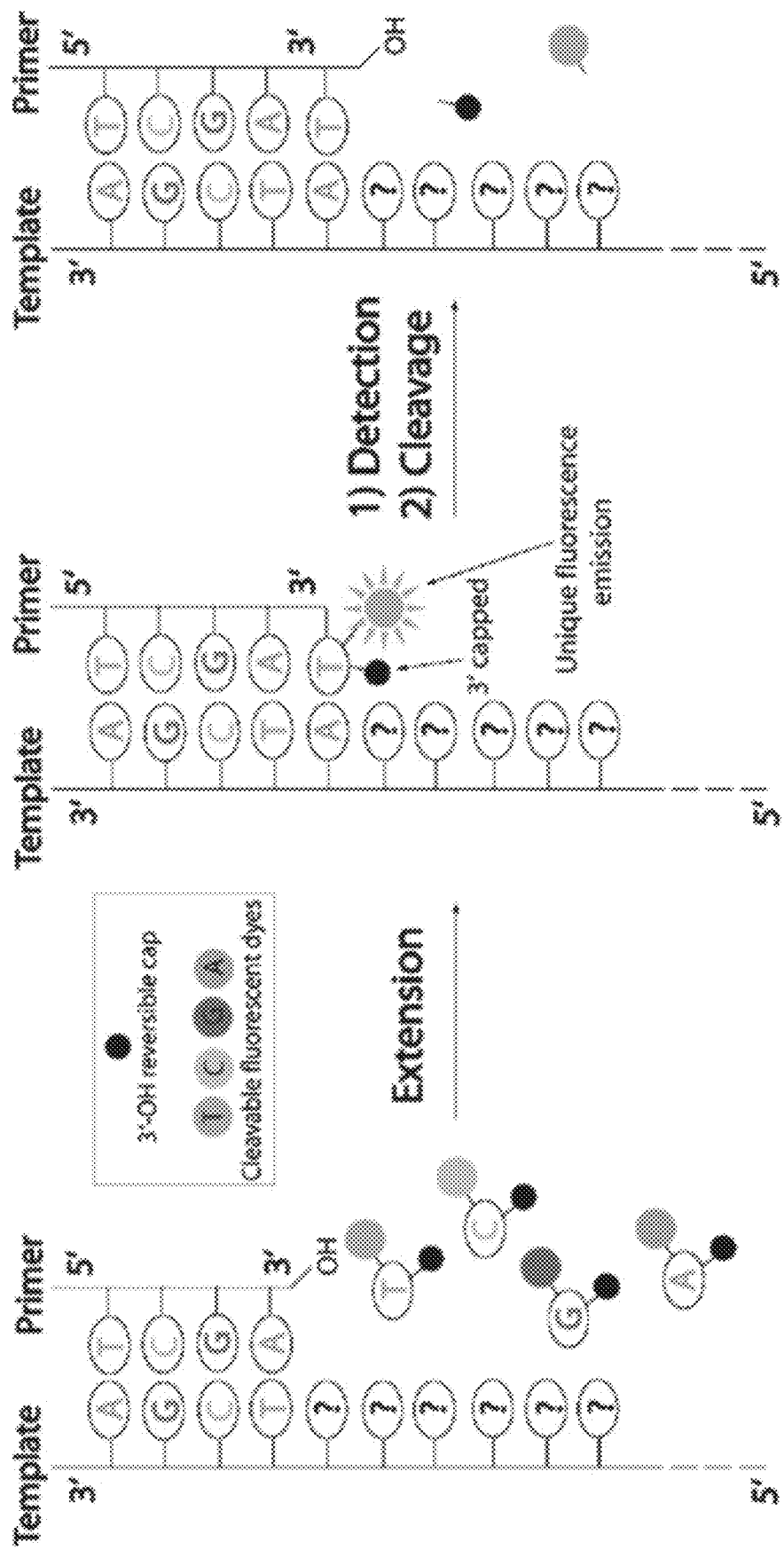
FIG. 14. Conceptual illustration of cyclic reversible termination based sequencing by synthesis. A target strand, typically a member of a micro-scale cluster of identical molecules amplified from a template, is primed with a sequencing primer which will initiate polymerase binding. A mixture of nucleotides modified with a fluorophore and a 3'blocking group are added along with a polymerase. The primer is extended by a single base and the cluster is imaged. The dye and the 3'blocking group are then both cleaved, and the cycle can be repeated.
Figure 15:
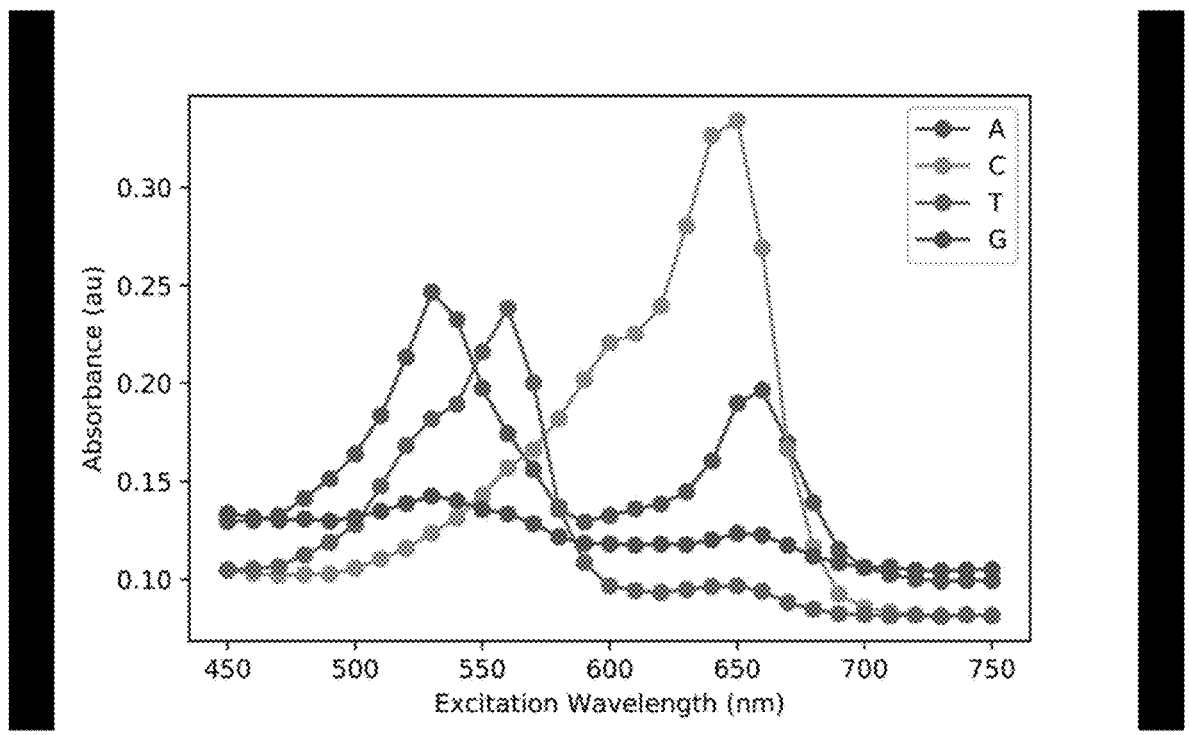
FIG. 15. Measurement of emission and absorption spectra for NextSeq dyes. (a) Absorption spectra for NextSeq dyes indicating two unique colors. (b) Emission spectra for an excitation close to each of the absorption maxima.
Figure 15:
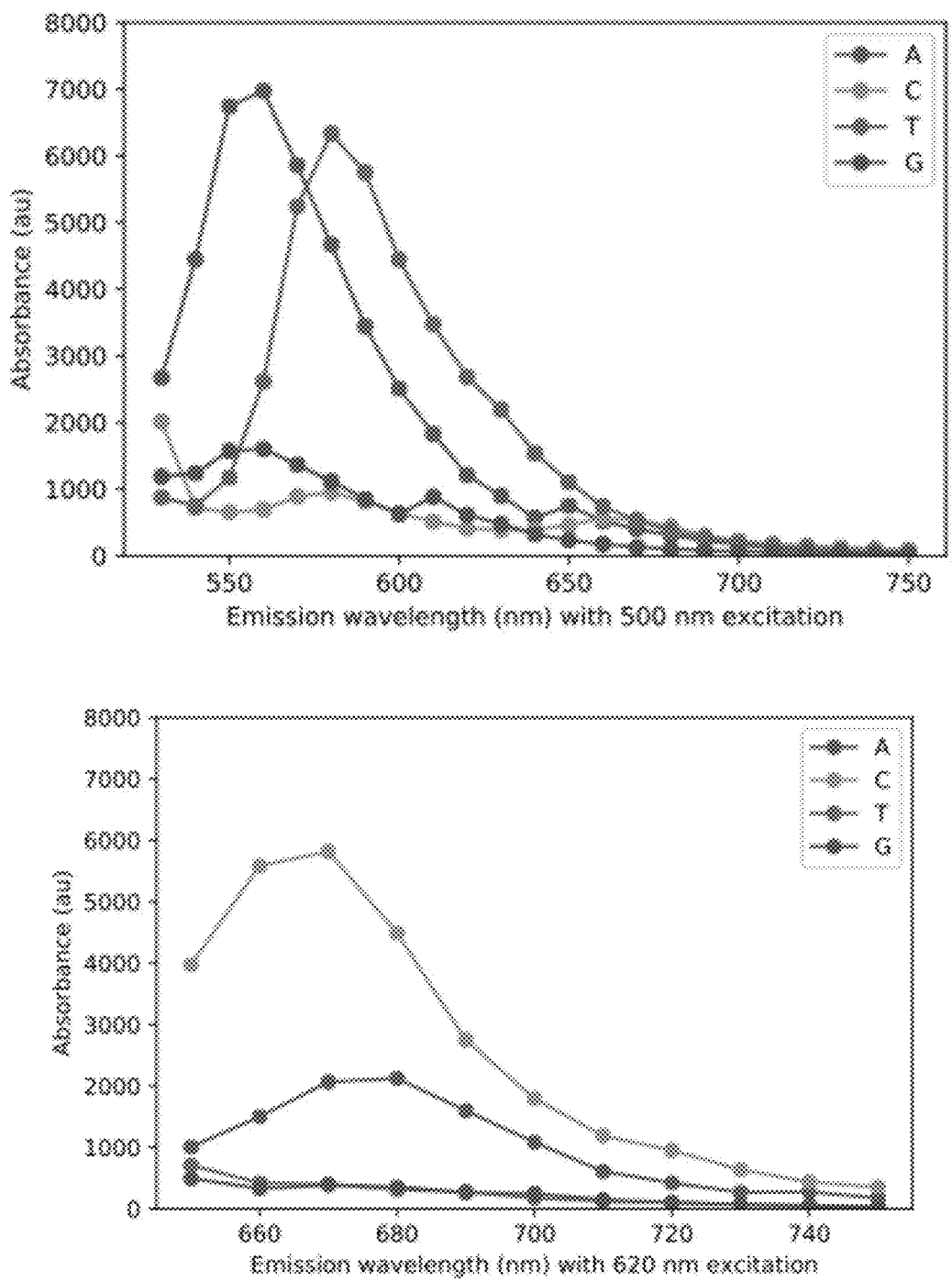

Seven cycles of imaging were performed, with two consecutive rounds of synthesis before each imaging cycle, on in situ RNA sequencing libraries prepared in hydrogel embedded and expanded rat neuron culture. Without wishing to be bound to any particular theory, it was hypothesized that multiple rounds of synthesis would increase dye addition efficiency and decrease phasing. A representative region of interest of a sample after the first imaging cycle is shown in FIG. 8. A crosstalk plot for the first base of sequencing is shown in FIG. 9. It was observed that the two components are not as well resolved as in the analogous case in Example Y: the two arms of the crosstalk plot have taken on a more conical shape as opposed to the sharply defined arms of FIG. 4, and the dataset is initially more correlated. However, after seven rounds of sequencing, as shown in FIG. 10, the crosstalk plot continues to maintain the same shape, and the correlation has not significantly increased. FIG. 11 shows that the correlation over all seven cycles of imaging is essentially constant. Similarly, FIG. 12 shows that the number of spots that pass an intensity threshold of 0.6 is also essentially constant over seven cycles of sequencing.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for amplifying one or more target RNAs in a fixed biological sample comprising:
   (a) contacting the sample with a small molecule linker or a nucleic acid adaptor comprising a binding moiety and an anchor, wherein the binding moiety binds to target nucleic acids in the sample; and wherein the anchor comprises a polymerizable moiety;
   (b) permeating the sample with a composition comprising precursors of a swellable material; and
   (c) initiating polymerization of the precursors of the swellable material to form a swellable material, wherein the swellable material is bound to the small molecule linker or a nucleic acid adaptor to form a sample-swellable material complex;
   (d) incubating the sample with a pair of polynucleotides complementary to non-overlapping and proximal sequences of a target RNA wherein the polynucleotides hybridize to the target RNA;
   (e) ligating the polynucleotide pair using a ligase; and
   (f) amplifying the ligation product.

2. The method of claim 1, further comprising expanding the sample.

3. The method of claim 2, wherein expanding the sample comprises adding an aqueous solvent or liquid to cause the sample-swellable material complex to swell, thereby physically expanding the complex.

4. The method of claim 2, wherein the biological sample is expanded prior to step (f) or post step (f).

5. The method of claim 1, wherein the swellable material is a polyelectrolyte gel.

6. The method of claim 1, wherein the pair of polynucleotides is hybridized to the target RNA in situ.

7. The method of claim 1, further comprising the step of sequencing the amplified ligation product within the sample.

8. A method for detecting one or more target RNAs in a fixed biological sample comprising:
 (a) contacting the sample with a small molecule linker or a nucleic acid adaptor comprising a binding moiety and an anchor, wherein the binding moiety binds to target nucleic acids in the sample; and wherein the anchor comprises a polymerizable moiety;
 (b) permeating the sample with a composition comprising precursors of a swellable material; and
 (c) initiating polymerization of the precursors of the swellable material to form a swellable material, wherein the swellable material is bound to the small molecule linker or a nucleic acid adaptor to form a sample-swellable material complex;
 (d) incubating the sample with a pair of polynucleotides complementary to non-overlapping and proximal sequences of a target RNA wherein the polynucleotides hybridize to the target RNA;
 (e) ligating the polynucleotide pair using a ligase;
 (f) amplifying the ligation product; and
 (g) detecting the amplified product.

9. The method of claim 8, further comprising expanding the sample.

10. The method of claim 9, wherein expanding the sample comprises adding an aqueous solvent or liquid to cause the sample-swellable material complex to swell, thereby physically expanding the complex.

11. The method of claim 9, wherein the biological sample is expanded prior to step (f) or post step (f).

12. The method of claim 8, wherein the swellable material is a polyelectrolyte gel.

13. The method of claim 8, wherein the pair of polynucleotides is hybridized to the target RNA in situ.

14. The method of claim 8, further comprising the step of localizing the amplified product within the fixed biological sample.

15. The method of claim 8, further comprising the step of sequencing the amplified ligation product within the fixed biological sample.

* * * * *

SEQUENCE LISTING

<160> NUMBER OF SEQ ID NOS: 5

<210> SEQ ID NO 1
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 1
gtactgaact gtctcttata cacatctgac gctgccgacg a                41

<210> SEQ ID NO 2
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 2
gtactgttct gtctcttata cacatctgac gctgccgacg a                41

<210> SEQ ID NO 3
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 3
gtactgccct gtctcttata cacatctgac gctgccgacg a                41

<210> SEQ ID NO 4
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 4
gtactgggct gtctcttata cacatctgac gctgccgacg a                41

<210> SEQ ID NO 5
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 5
tcgtcggcag cgtcagatgt gtataagaga cag                         33